United States Patent
Huang et al.

(10) Patent No.: US 9,907,818 B2
(45) Date of Patent: *Mar. 6, 2018

(54) METHODS OF TREATING A TREATMENT-RESISTANT GASTROINTESTINAL SPASM

(71) Applicant: LiveLeaf, Inc., San Carlos, CA (US)

(72) Inventors: Alexander L Huang, Menlo Park, CA (US); Gin Wu, San Rafael, CA (US)

(73) Assignee: LIVELEAF, INC., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/432,478

(22) Filed: Feb. 14, 2017

(65) Prior Publication Data

US 2018/0000862 A1   Jan. 4, 2018

Related U.S. Application Data

(63) Continuation of application No. 15/199,075, filed on Jun. 30, 2016, now Pat. No. 9,603,883, which is a
(Continued)

(51) Int. Cl.
 *A61K 33/40* (2006.01)
 *A61K 45/06* (2006.01)
 (Continued)

(52) U.S. Cl.
 CPC ............ *A61K 33/40* (2013.01); *A61K 31/192* (2013.01); *A61K 31/352* (2013.01);
 (Continued)

(58) Field of Classification Search
 CPC ...... A61K 33/40; A61K 45/06; A61K 31/192; A61K 31/7048; A61K 31/352;
 (Continued)

(56) References Cited

U.S. PATENT DOCUMENTS

| 1,844,018 A | 4/1929 | Sailer |
| 1,891,149 A | 12/1930 | Elger |

(Continued)

FOREIGN PATENT DOCUMENTS

| CN | 1079393 | 12/1993 |
| CN | 1922996 | 3/2007 |

(Continued)

OTHER PUBLICATIONS

U.S. Appl. No. 61/009,484, Huang,et al.—related case Publicly available in Application 2013/0078322, Dec. 28, 2007.
(Continued)

*Primary Examiner* — Trevor Love
(74) *Attorney, Agent, or Firm* — Brian S. Boyer; Syndicated Law, PC

(57) ABSTRACT

Methods of treating a gastrointestinal spasm in a subject are provided. The methods can include administering an effective amount of a formulation to treat the gastrointestinal spasm, the formulation having a tannin combined with a hydrogen donor in a pharmaceutically acceptable excipient as a binding pair, the tannin releasing in an oxidized state from the hydrogen donor after oral administration of the formulation in the subject; wherein, the composition at least inhibits a gastrointestinal spasm in the subject when compared to a second subject in a control group in which the composition was not administered.

21 Claims, 4 Drawing Sheets

Related U.S. Application Data continuation of application No. 14/745,426, filed on Jun. 20, 2015, now Pat. No. 9,408,869, which is a continuation of application No. 14/662,725, filed on Mar. 19, 2015, now Pat. No. 9,089,596, which is a continuation of application No. 14/584,419, filed on Dec. 29, 2014, now Pat. No. 9,023,895, which is a continuation of application No. 14/317,970, filed on Jun. 27, 2014, now Pat. No. 8,946,304, which is a continuation of application No. 14/272,047, filed on May 7, 2014, now Pat. No. 8,809,399, which is a continuation of application No. 14/222,605, filed on Mar. 22, 2014, now Pat. No. 8,772,352, which is a continuation of application No. 14/173,079, filed on Feb. 5, 2014, now Pat. No. 8,772,350, which is a continuation of application No. 14/142,895, filed on Dec. 29, 2013, now Pat. No. 8,716,353, which is a continuation of application No. 13/726,180, filed on Dec. 23, 2012, now Pat. No. 8,716,351.

(51) Int. Cl.

| | | |
|---|---|---|
| *A61K 31/192* | (2006.01) | |
| *A61K 31/7048* | (2006.01) | |
| *A61K 31/352* | (2006.01) | |
| *A61K 36/185* | (2006.01) | |
| *A61K 36/82* | (2006.01) | |
| *A61K 36/22* | (2006.01) | |
| *A61K 31/7028* | (2006.01) | |
| *A61K 31/7034* | (2006.01) | |
| *A61K 31/353* | (2006.01) | |

(52) U.S. Cl.
CPC ........ *A61K 31/353* (2013.01); *A61K 31/7028* (2013.01); *A61K 31/7034* (2013.01); *A61K 31/7048* (2013.01); *A61K 36/185* (2013.01); *A61K 36/22* (2013.01); *A61K 36/82* (2013.01); *A61K 45/06* (2013.01)

(58) Field of Classification Search
CPC ...... A61K 36/185; A61K 36/82; A61K 36/22; A61K 31/7028; A61K 31/7034; A61K 31/353
See application file for complete search history.

(56) References Cited

U.S. PATENT DOCUMENTS

| | | | |
|---|---|---|---|
| 1,965,458 A | 5/1932 | Elger | |
| 3,484,248 A | 12/1969 | Graham et al. | |
| 3,649,297 A | 3/1972 | Millin | |
| 3,692,904 A | 9/1972 | Tsutsumi | |
| 3,817,835 A | 6/1974 | Neidleman | |
| 3,821,440 A | 6/1974 | Reeve | |
| 3,824,184 A | 7/1974 | Hatcher et al. | |
| 3,860,694 A | 1/1975 | Jayawant | |
| 3,864,454 A | 2/1975 | Pistor et al. | |
| 4,008,339 A | 2/1977 | Matsuda et al. | |
| 4,072,671 A | 2/1978 | Sodini et al. | |
| 4,171,280 A | 10/1979 | Maddox et al. | |
| 4,435,601 A | 3/1984 | Formanek et al. | |
| 4,472,302 A | 9/1984 | Karkhanis | |
| 4,472,602 A | 9/1984 | Bordelon et al. | |
| 4,514,334 A | 4/1985 | Mark | |
| 4,623,465 A | 11/1986 | Klibanov | |
| 4,829,001 A | 5/1989 | Mencke et al. | |
| 4,900,671 A | 2/1990 | Pokora et al. | |
| 4,966,762 A | 10/1990 | Pfeffer et al. | |
| 5,008,248 A | 4/1991 | Bywater et al. | |
| 5,141,611 A | 8/1992 | Ford | |
| 5,208,010 A | 5/1993 | Thaler | |
| 5,231,193 A | 7/1993 | Mizusawa et al. |
| 5,260,021 A | 11/1993 | Zeleznick |
| 5,296,376 A | 3/1994 | Bridges et al. |
| 5,328,706 A | 7/1994 | Endico |
| 5,389,369 A | 2/1995 | Allen |
| 5,614,501 A | 3/1997 | Richards |
| 5,653,746 A | 8/1997 | Schmitt |
| 5,661,170 A | 8/1997 | Chodosh |
| 5,700,769 A | 12/1997 | Schneider et al. |
| 5,756,090 A | 5/1998 | Allen |
| 5,824,414 A | 10/1998 | Kobayashi et al. |
| 5,834,409 A | 11/1998 | Ramachandran et al. |
| 5,839,369 A | 11/1998 | Chatterjee et al. |
| 5,879,733 A | 3/1999 | Ekanayake et al. |
| 5,891,440 A | 4/1999 | Lansky |
| 6,068,862 A | 5/2000 | Ishihara et al. |
| 6,071,541 A | 6/2000 | Murad |
| 6,080,573 A | 6/2000 | Convents et al. |
| 6,136,849 A | 10/2000 | Hoffmann et al. |
| 6,284,770 B1 | 9/2001 | Mangel et al. |
| 6,296,880 B1 | 10/2001 | Murad |
| 6,297,273 B1 | 10/2001 | Romanczyk et al. |
| 6,383,523 B1 | 5/2002 | Murad |
| 6,420,148 B2 | 7/2002 | Yamaguchi |
| 6,436,342 B1 | 8/2002 | Petri et al. |
| 6,444,805 B1 | 9/2002 | Sohn et al. |
| 6,537,546 B2 | 3/2003 | Echigo et al. |
| 6,551,602 B1 | 4/2003 | Barrett et al. |
| 6,630,163 B1 | 10/2003 | Murad |
| 6,642,277 B1 | 11/2003 | Howard et al. |
| 6,926,881 B2 | 8/2005 | Hirose et al. |
| 6,936,580 B2 | 8/2005 | Sherry |
| 7,018,660 B2 | 3/2006 | Murad |
| 7,241,461 B2 | 7/2007 | Myhill et al. |
| 7,297,344 B1 | 11/2007 | Fleischer et al. |
| 7,341,744 B1 | 3/2008 | Rozhon et al. |
| 7,504,251 B2 | 3/2009 | Olshenitsky et al. |
| 7,972,635 B2 | 7/2011 | Seabrook et al. |
| 8,007,771 B2 | 8/2011 | Ramji et al. |
| 8,067,041 B2 | 11/2011 | Quart et al. |
| 8,343,552 B2 | 1/2013 | Huang et al. |
| 8,586,110 B2 | 11/2013 | Huang et al. |
| 8,716,351 B1 | 5/2014 | Huang et al. |
| 8,716,352 B1 | 5/2014 | Huang et al. |
| 8,716,353 B1 | 5/2014 | Huang et al. |
| 8,722,040 B2 | 5/2014 | Huang et al. |
| 8,722,116 B2 | 5/2014 | Huang et al. |
| 8,734,867 B2 | 5/2014 | Huang et al. |
| 8,765,818 B1 | 7/2014 | Huang et al. |
| 8,772,350 B1 | 7/2014 | Huang et al. |
| 8,772,351 B1 | 7/2014 | Huang et al. |
| 8,772,352 B1 | 7/2014 | Huang et al. |
| 8,790,640 B1 | 7/2014 | Huang et al. |
| 8,809,399 B1 | 8/2014 | Huang et al. |
| 8,822,544 B2 | 9/2014 | Huang et al. |
| 8,822,545 B1 | 9/2014 | Huang et al. |
| 8,916,539 B2 | 12/2014 | Yedgar et al. |
| 8,946,304 B2 | 2/2015 | Huang et al. |
| 8,952,072 B2 | 2/2015 | Huang et al. |
| 9,023,895 B1 | 5/2015 | Huang et al. |
| 9,089,596 B1 | 7/2015 | Huang et al. |
| 9,192,635 B2 | 11/2015 | Huang et al. |
| 9,408,869 B2 | 8/2016 | Huang et al. |
| 9,603,871 B2 | 3/2017 | Huang et al. |
| 9,603,883 B2 | 3/2017 | Huang et al. |
| 9,636,361 B2 | 5/2017 | Huang et al. |
| 2001/0007762 A1 | 7/2001 | Echigo et al. |
| 2002/0034553 A1 | 3/2002 | Zayas |
| 2002/0041901 A1 | 4/2002 | Murad |
| 2002/0172719 A1 | 11/2002 | Murad |
| 2003/0059396 A1 | 3/2003 | Bhakoo et al. |
| 2003/0078212 A1 | 4/2003 | Li et al. |
| 2003/0228379 A1 | 12/2003 | Shi et al. |
| 2004/0013710 A1 | 1/2004 | Howell |
| 2004/0022863 A1 | 2/2004 | Hamtini |
| 2004/0137077 A1 | 7/2004 | Ancira et al. |
| 2004/0228831 A1 | 11/2004 | Belinka, Jr. et al. |
| 2005/0169988 A1 | 8/2005 | Tao et al. |
| 2005/0175658 A1 | 8/2005 | DiMauro et al. |

(56) References Cited

U.S. PATENT DOCUMENTS

| | | |
|---|---|---|
| 2006/0024339 A1 | 2/2006 | Murad |
| 2006/0024385 A1 | 2/2006 | Pedersen |
| 2006/0051429 A1 | 3/2006 | Murad |
| 2006/0105069 A1 | 5/2006 | Moffett et al. |
| 2006/0165812 A1 | 7/2006 | Charron |
| 2006/0292255 A1 | 12/2006 | Moffett et al. |
| 2007/0010632 A1 | 1/2007 | Kaplan et al. |
| 2007/0078107 A1 | 4/2007 | Yedgar et al. |
| 2007/0110812 A1 | 5/2007 | Xia et al. |
| 2007/0154414 A1 | 7/2007 | Bonfiglilio |
| 2007/0178055 A1 | 8/2007 | Buch et al. |
| 2007/0187429 A1 | 8/2007 | Farahmand |
| 2007/0275104 A1 | 11/2007 | Kornman et al. |
| 2008/0003314 A1 | 1/2008 | Ochiai et al. |
| 2008/0008665 A1 | 1/2008 | Ramji et al. |
| 2008/0118602 A1 | 5/2008 | Narayanan et al. |
| 2008/0175812 A1 | 7/2008 | Seabrook et al. |
| 2008/0253976 A1 | 10/2008 | Scott et al. |
| 2009/0023804 A1 | 1/2009 | Baugh et al. |
| 2009/0048312 A1 | 2/2009 | Greenberg et al. |
| 2009/0083885 A1 | 3/2009 | Daniell |
| 2009/0093440 A1 | 4/2009 | Murad |
| 2010/0055138 A1 | 3/2010 | Margulies et al. |
| 2010/0278759 A1 | 11/2010 | Murad |
| 2012/0136019 A1 | 5/2012 | Boyd et al. |
| 2012/0328711 A1 | 12/2012 | Huang et al. |
| 2012/0329736 A1 | 12/2012 | Huang et al. |
| 2014/0072655 A1 | 3/2014 | Huang et al. |
| 2014/0072660 A1 | 3/2014 | Huang et al. |
| 2014/0161902 A1 | 6/2014 | Huang et al. |
| 2014/0227367 A1 | 8/2014 | Huang et al. |
| 2016/0074435 A1 | 3/2016 | Huang et al. |
| 2017/0112877 A1 | 4/2017 | Huang et al. |

FOREIGN PATENT DOCUMENTS

| | | |
|---|---|---|
| CN | 1939468 | 4/2007 |
| CN | 101260129 | 9/2008 |
| CN | 200910167930.5 | 10/2009 |
| CN | 102421891 | 4/2012 |
| EP | 0390107 | 10/1990 |
| EP | 0797451 | 9/2004 |
| EP | 1736165 | 12/2006 |
| GB | 1204576 | 9/1970 |
| JP | 2005-509588 | 5/1995 |
| JP | 1987126130 | 11/1995 |
| JP | 2011-043696 | 7/1997 |
| JP | 2000-026310 | 3/1999 |
| JP | 2005-519151 | 2/2002 |
| JP | 2005-533027 | 5/2002 |
| JP | 2002238554 | 8/2002 |
| JP | 2004-510717 | 1/2004 |
| JP | 2007-531771 | 4/2004 |
| JP | 2006-045121 | 8/2004 |
| JP | 2006-182727 | 12/2004 |
| JP | 2008-542286 | 5/2005 |
| JP | 2008-072961 | 9/2006 |
| JP | 2008-143808 | 6/2008 |
| JP | 2015-146637 | 1/2016 |
| KR | 2004056061 | 6/2004 |
| KR | 20050028755 | 3/2005 |
| KR | 2008101005 | 11/2008 |
| WO | WO 1994/003607 | 2/1994 |
| WO | WO 2000/061166 | 4/1999 |
| WO | WO 2000/006116 | 2/2000 |
| WO | WO 2004/003607 | 1/2004 |
| WO | WO 2005/067727 | 7/2005 |
| WO | WO 2005/099721 | 10/2005 |
| WO | WO 2006/029484 | 3/2006 |
| WO | WO 2006/038893 | 4/2006 |
| WO | WO 2006/096778 | 11/2006 |
| WO | WO 2007/003068 | 1/2007 |
| WO | WO 2010/018418 | 2/2010 |
| WO | WO 2010/101844 | 9/2010 |
| WO | WO 2010/138082 | 12/2010 |
| WO | WO 2012/178127 | 12/2012 |
| WO | WO 2013/181331 | 5/2013 |
| WO | WO 2014/099686 | 6/2014 |
| WO | WO 2015/192136 | 12/2015 |

OTHER PUBLICATIONS

U.S. Appl. No. 61/209,260, Huang,et al.—related case Publicly available in Application 2013/0078322, Mar. 4, 2009.

U.S. Appl. No. 14/304,812, Huang,et al.—related case, Jun. 13, 2014.

U.S. Appl. No. 15/463,992, Huang,et al.—related case, Dec. 28, 2007.

European search report for EP 10749160, dated Sep. 10, 2013.

European search report for EP 12802538, dated Apr. 30, 2014.

European search report for EP 13865735.8, LiveLeaf, Inc.—related case.

English translated office action for JP2011553012, Mar. 17, 2014, Shinsuke Aramaki.

International Search Report for PCT/US2010/025805, dated Aug. 15, 2013, Metaactiv, Inc.

International Search Report for PCT/US2012/043900, dated Jan. 30, 2013, LiveLeaf, Inc.—related case.

International Search Report for PCT/US2015/035842, dated Oct. 29, 2015, LiveLeaf, Inc.—related case.

Intellectual Property Office of Singapore Written Opinion for 2013093489, dated Aug. 14, 2015.

A technical journal on food chemistry & chemicals 21(11) 2005. See cite No. 125, reference No. 12 on English translated office action for JP2011-553012 for relevance.

Absolute Astronomy, Catechin, The Source of this article is Wikipedia,http://en.wikipedia.org/w/index.php?title=Catechin &oldid=77274034, Jan. 2008, 5 pages.

Agnivesa, Caraka Samhita, Edited & translated by P.V. Sharma, vol. II: Chaukhamba Orientalia, Varanasi, Edn, $5^{th}$, 2000. [ time of origin 1000 BC—$4^{th}$ century] p. 418.

Ahmad,I, et al: Antimicrobial and Phtochemical studies on 45 Indian medicinal plants against multi-drug resistant human pathogens, Journal of Ethnopharmacology: 74: 113-123: (2001).

Ahn, Y., et al. Tea polyphenols: selective growth inhibitors of Clostridium spp. Agric. Biol. Chem. 55(5): 1425-1426 (1991).

Akagawa et al. Production of hydrogen peroxide by polyphenols and polyphenol-rich beverages undequasi-physiological conditions. Bioscience Biotechnol Biochem. 67(12): 2632-2640 (Sep. 2003).

Akiyama et al. Antibacterial action of several tannins against *Staphylococcus aureus*, Journal of Antimicrobial Chemotherapy. 48, 487-491 (Jan. 2001).

Alfa, et al. Improved eradication of clostridium difficile spores from toilets of hospitalized pstents using an accelerated hydrogen peroxide as the cleaning agent. BMC infectious diseases 10: 268 (2010). Online URL: http://www.biomedcentral.com/1471-2334/10/265 (downloaded Mar. 19, 2015).

Aoshima et al. Antioxidative and Anti-hydrogen Peroxide Activities of Various Herbal Teas. Department of Chemistry, Faculty of Science, Yamaguchi University. 1677-1 Yoshida, Yamaguchi 753-8512, 1 page. Japan, (Available online Oct. 2, 2006).

Asquith, T.N., et al. Interactions of condensed tannins with selected proteins, Phytochemistry, 25, 1591-1593 (1986).

Avdiushko, S.A., et al. Detection of several enzymatic activities in leaf prints of cucumber plant. Physiological and Molecular Plant Pathology 42, 441-454 (1993).

Azim T, et al. Lipopolysaccharid-specific antibodies in plasma and stool of children with shigella-associated leukemoid reaction andhemolytic-uremic syndrome. Clin diagn lab immunol 3(6): 701-705 (1996).

Baeuerle, P.A. Reactive oxygen intermediates as second messengers of a general pathogen response. Pathol Biol. 44(1): 29-35 (1996).

Bailey, et al. Regulation of mucosal immune responses in effector sites. Proc Nutr Soc 60: 427-435 (2001).

Barroso. J.B. et al. Localization of nitric-oxide synthase in plant peroxisomes. The Journal of Biological Chemistry 274(51): 36729-36733 (1999).

(56) References Cited

OTHER PUBLICATIONS

BBC. Denaturing of enzymes. http://www.bbc.co.uk/schools/gcsebitesize/science/add_edexcel/cells/enzymesrev3.shtml (2006).
Berglin, E. H. et al. Potentiation by L-Cysteine of the bactericidal efffect of hydrogen peroxide in Escherichia coli J. Bacteriol 152(1): 81-88 (1982).
Berglin, E. H. et al. Potentiation by sulfide of hydrogen peroxide-induced killing of Escherichia coli. Infection and Immunity, 49(3), pp. 538-543 (1985).
Bernays, E.A. et al. Herbivores and plant tannins. Advances in Ecological Research, 19, 263-302 (1989).
Bhavamisra; Bhavaprakasa. Edited & translated by Brahmasankara Misra, Part II: Chaukhamba Sanskrit Sansthan, Varanasi, Edn $7^{th}$, 474 2000. [Time of orgin $16^{th}$ centuty].
Bialonska, et al. Urolithias, intestinal microbial metabolites of pomegranate ellagitannins exhibit antioxidant activity in a cell-based assay. J Agric Food Chem 57: 10181-10186 (2009).
Biasi, et al. Polyphenol supplementation as a complementary medicinal approach to treating inflammatory bowel disease. Curr Med Chem 18: 4851-4865 (2011).
Biesalaki, H.K. Polyphenols and inflammation: basic interactions. Curr Opin Clin Nutr Metab Care 10: 724-728 (2007).
Bittner, When quinones meet amino acids: chemical, physical, and biological consequences. Amino Acids, 30, 205-224, Apr. 13, 2006.
Birdi, et al. Newer insights into the mechanism of action of Psidum guajava L. leaves in infectious diarrhea. BMC complement altern med 10: 33 (2010).
Blair, T.S. Botanic drugs their materia medica, pharmacology and therapeutics. The Therapeutic Digest Publishing Company, Cincnnati, Ohio, 20 pages Jan. 1917.
Bontempo, et al. Effects of a novel plant extract administred through drinking water on the post-weaning gut health of piglets. Submitted to J Anim Sci Jun. 2012.
Boudry, et al. Weaning induces both transient and long-lasting modifications of absorptive, secretory, and barrier properties of piglet intestine. J Nutr 134: 2256-2262 (2004).
Bowditch, M. I. et al. Ascorbate free-radical reduction by glyoxysomal membranes, Plant Physiology 94: 531-537 (1990).
Bowler, C. et al. Superoxide dismutase and stress tolerance. Annu Rev Plant Physiol Plant Mol Biol 43: 83-116 (1992).
Bowler, C., et al. Superoxide dismutase in plants. Crit Rev Plant Sci, 13(3): 199-218 (1994).
Bravo, L. Polyphenols : chemistry, dietary sources, metabolism, and nutritional significance : Nutrition Revievs 56 : 317-333 : 1998.
Breusegem, F.V. et al. The role of active oxygen species in plant signal transduction. Plant Science 161: 405-414 (2001).
Brown, et al. Outcomes of diarrhea management in operations Iraqi Freedom and Enduring Freedom. Travel med infect dis 7: 337-343 (2009).
Bruins, et al. In vivo and in vitro effects of tea extracts on enterogoxigenic Escherihia coli-induced instestinal fluid loss in animal models. J Pediatr Gastroenterol Nutr 43: 459-469 (2006).
Buchanan-Wollaston, V. The molecular biology of leaf senescence. J. Exp. Bot 48(2): 181-199 (1997).
Buck, A.E. A Reference Handbook of the Medical Sciences; vol. 5, William Wood & Company, New York: 253-255 (1887).
Bunkelmann, J.R. et al. Ascorbate peroxidase: A prominent membrane protein in oilseed glyoxysomes. Plant Physiol 110(2): 589-598 (1996).
Butler, E., et al. The role of lysyl oxidase and collagen crosslinking during sea urchin development. Exp Cell Res (173): 174-182 (1987).
Butler, L.G., et al. Interaction of proteins with sorghum tannin: mechanism, specificity and significance. Journal of the American Oil Chemists' Society 61(5): 916-920 (1984).
Chemtutor Solutions, [online] http://www.chemtutor.com/solution.htm, 11 pages. May 8, 1998, [retrieved from the internet archive Wayback Machine using internet URL http://wayback.archive.org/web/*/http://www.chemtutor.com/solution.htm].
Cheng, et al. Progress in studies on the antimutagenicity and anticarcinogenicity of green tea epicatechins. Chin. Med. Sci. J. 6(4): 1 page (abstract) (Dec. 1991).
Cheng, H.Y., et al. Antiherpes simplex virus type 2 activity of casuarinin from the bark of terminalia arjuna linn. Antiviral Research 55(3): 447-455 (2002).
Chung,K.T, et.al.: Tannis and human health: A review: Clinical Reviews in Food Science and Nutrition: 38(6): 421-464: (1998).
Cichoke, A.J. The Complete Book of Enzyme Therapy:Penguin Putnam Inc., New York, NY: 69 (1999).
Clyde E.H. Effects of temperature on catalase activity. Ohio Journal of Sceince 50(6): 273-277 (Nov. 1950).
Coates, et al. Molecular defects in serotonin content and decreased serotonin reuptake transporter in ulcerative colitis and irritable bowel syndrome. Gastroenterology 126(7): 1657-1664 (2004).
Cordeiro, C., et al. Antibacterial efficacy of gentamicin encapsulated in ph-sensitive liposomes against an in vivo salmonella enteric serovar typhimurium intracelliular infection model. Antimicrobial agents and Chemotherapy 44(3): 533-539 (2000).
Corpas, F.J., et al. A role for leaf peroxisomes in the catabolism of purines. J. Plant Physiol 151: 246-250 (1997).
Corpas, F.J., et al. Copper-Zinc superoxide dismutase is a constituent enzyme of the matrix of peroxisomes in the cotyledons of oilseed plants. New Phytol 138(2): 307-314 (1998).
Cotton, S. Hydrogen peroxide. http://www.chrn.bris.ac.yk/motm/h2o2/h2o2v.htm p. 1-7 (2006).
Croft, K.D. The chemistry and biological effects of flavonoids and phenolic acids. Annals of the New York Academy of Sciences 845: 435-442. (1998).
Daayf et al. Recent advances in polyphenol research. Blackwell publishing 264: 3. (2008).
Dayan et al. Oleic acid-induced skin penetration effects of a lamellar delivery system excerpt (Cosmetics & Toiletries Magazine. Cosmetics and Toiletries.com, http://www.cosmeticsandtoiletries.com/formulating/ingredientldelivery/9496857.html , 2 pages (Aug. 31, 2007).
Dec, J. et al. Use of plant material for the decontamination of water polluted with phenols. Biotechnology and Bioengineering 44: 1132-1139. (1994).
De Paepe, K., et al. Repair of acetone and sodium lauryl sulphate-damaged human skin barrier function using topically applied emulsions containing barrier lipids. Journal of European Academy of Dermatology & Venereology 1 page (abstract) (Nov. 2002).
Desnoeck et al. Reducing sour in commercial pig farms with a novel plant extract-results of veterinary field trials. Poster presentation at international symposium on alternatives to antibiotics. Program to Alternatives to antibiotics (ATA). The world organization for animal health, Paris, France:78 (Sep. 25-28, 2012.).
Definition of "Compound" and "Composition". Grant and Hackh's Chemical Dictionary, $5^{th}$ Ed. McGraw Hill 2 pages (1987).
Dell'Agli, M., et al. Ellagitannins of the fruit rind of pomegranate (Punica granatum) antagonize in vitro the host inflammatory response mechanisms involved in the onset of malaria. Malaria Journal 9(208): 1-9. Specif. p. 1,2 (2010).
Del Río, L.A., et al. Metabolism of oxygen radicals in peroxisomes and cellular implications. Free Radical Biol Med 13(5): 557-580 (1992).
Del Río, L.A., et al. Peroxisomes as a source of superoxide and hydrogen peroxide in stressed plants. Biochem Soc Trans 24: 434-438 (1996).
Del Rio, L.A., et al. The activated oxygen role of peroxisomes in senescence. Plant Physiol. 116(4): 1195-1200 (1998).
Del Rio, D., et al. HPLC-MS$^n$ analysis of phenolic compounds and purine alkaloids in green and black tea. J Agric Food Chem 52: 2807-2815 (2004).
Denaturation of Proteins. http://chemistry.elehurst.edu/vchembook/568denaturation.html (2016).
Denes, et al. Minimal inhibitory concentration of a noval plant extract on growth of bacterial isolates with veteriany importance. Poster presentation at international symposium on alternatives to antibiotics. Program to Alternatives to antibiotics (ATA). The world organization for animal health, Paris, France:33 (Sep. 25-28, 2012.).

(56) References Cited

OTHER PUBLICATIONS

Do-It-Yourself Health. Editor: R. Somerville, Time Life Books 2 pages (1997).
Doke, N., et al. The oxidative burst protects plants against pathgen attack: mechanism and role as an emergency signal for plant bio-defence. Gene 179(1): 45-51(1996).
Domeneghini, et al. Gut topic feed additives and their effects upon the gut structure and intestinal metabolism. State of the art in the pig, and perspectives towards humans. Histol Histopathal 21: 273-883 (2006).
Drugs in Japan 2004 Jiho Inc. 494 (2003) See cite No. 125, reference No. 11 on English translated office action for JP2011-553012 for relevance.
Dudley et al. Cysteine as an inhibitor of polyphenol oxidase. Journal of Food Biochemistry 13(1): 1 page (abstract) (Feb. 23, 2007).
Efskind, P.S. et al. A double-blind placebo-controlled trail with loperamide in irritable bowel syndrome. Scand J. Gastroenterol 31:463-468 (1996) Abstract.
El Amin, F.M., et al. Genetic and environmental effects upon reproductive performance of holstein crossbreds in the sudan. Dairy Sci 69: 1093-1097 (1986).
Elstner, E.F., et al. Mechanisms of oxygen activation during plant stress, proceedings of the royal society of Edinburgh. B Biology 102B: 131-154 (1994).
Fang, T.K., et al. Electron transport in purified glyoxysomal membranes from castor bean endosperm. Planta 172(1): 1-13 (1987).
Faure, et al. Serotonin signaling in alterad irritable bowel syndrome with diarrhea but not in functional dyspepsia in pediatric patients. Gastroenterology 139(1): 249-258 (2010).
FDA. The judicious use of medically important antimicrobial drugs in food-producing animals. U.S. Government Printing Office Washington, DC, 26 pp (2012).
Feldman et al. Binding affinities of gallotannin analogs with bovine serum albumin: ramifications for polyphenol-protein molecular recognition. Phytochemistry 51, Elsevier Science Ltd 867-872 (Jan. 1999).
Food processing 43(6): 44-58 (2008). See cite No. 125, reference No. 15 on English translated office action for JP2011-553012 for relevance.
Fridovich, I. Superoxide Dismutases. Adv Enzymol Relat Areas Mol Biol. 58: 61-97 (1986).
Funatogawa, K., et al. Antibacterial activity of hydrolysable tannins derived from medicinal plants against helicobacter pylori. Microbiol Immunol 48(4): 251-261 (2004).
Gallily, R., et al. Non-immunological recognition and killing of xenogeneic cells by macrophages III. Destruction of fish cells by murine macrophages. Dev Comp Immunol 6(3): 569-578 (1982).
Gallochem Co., Ltd. Gallotannin, http://www.gallochem.com/Gallochem I.htm, 4 pages. (Jan. 2002).
Gan, S., et al. Making Sense of senescence, molecular genetic regulation, and manipulation of leaf senescence. Plant Physiol 113: 313-319 (1997).
Gee, J.M., et al. Polyphenolic compounds: Interactions with the gut and implications for human health. Current medicinal chemistry 8(11) 1245-1255 (2001).
Ghosh, A., et al. Antibacterial activity of some medicinal extracts. J Nat Med 62: 259-262 (2008). See cite No. 125, reference No. 14 on translated office actionfor JP2011-553012 for relevance.
Gilani, et al. Antispasmodic Effects of Rooibos Tea (*Aspalathus linearis*) is Mediated Predominantly through K+-Channel Activation. Basic & Clinical Pharmacology & Toxicology 99: 365-373 (2006).
Glossary of Medical Eduction Terms. (Online) URL: http://www.iime.org/glossary.htm [retrived on Mar. 24, 2011].
Goel et al. Xylanolytic Activity of ruminal *Streptococcus bovis* in presence of tannic acid. Annals of Microbiology 55(4): 295-297 (Jan. 2005).
Grabber, Mechanical maceration divergently shifts protein degradability in condensed-tannin vso-quinone containing conserved forages. Crop Science 48: 2 pages (Mar. 19, 2008).
greentealovers.com, Green Tea, White Tea: Health Catechin, (Online) URL: http://greentealovers.com/greenteahealthcatechin.htm#catechin, pp. 1-13 [Accessed Feb. 9, 2010].
Gulcin, et al. Radical scavenging and antioxidant activity of tannic acid. Arabian Journal of Chemistry 3: 43-53 (2010).
Guo et al. Studies on protective mechanisms of four components of green tea polyphenols against lipid peroxidation in synaptosomes. Biochim. Biophys. Acta, 1304(3): 1 page (abstract) (Dec. 13, 1996).
Guo, et al. Evaluation of antioxidant activity and preventing dna damage effect of pomegrante extracts by chemiluminescence method. J Agric Food Chem 55: 3134-3140 (2007).
Hadley. S.K., et al. Treatment of Irritable Bowel Syndrome. Am Fam Physician 75(12) 2501-2508 (2005).
Hagerman, Tannin Chemistry. Oxford, OH, 116 pages (Jan. 1998).
Hagerman, A.E., et al. The specificity of proanthocyanidin-protein interactions. Journal of Biological Chemistry 256(9): 4494-4497 (1981).
Hagerman, A.E., et al. Specificity of Tannin-Binding Salivary Proteins Relative to Diet Selection by Mammals. Canadian Journal of Zoology 71: 628-633 (1992).
Halwani, M., et al. Bactericidal efficacy of liposomal aminoglycosides against burkholderia cenocepacia. Journal of Antimicrobial Chemotherapy 60: 760-769 (2007).
Hamman. Composition and application of aloe vera leaf gel. Mocecules 13: 1599-1610 (2008).
Hanauer, et al. Randomized, double-blind, placebo-controlled clinical trial of loperamide plus simethicone versus loperamide alone and simethicone alone in the treatment of acute diarrhea with gas-related abdominal discomfort. Curr med res opin 23(5): 1033-1043 (2007).
Hara-Kudo, Y., et al. Antibactreial action on pathogenic bacterial spore by green tea catechins. Journal of the science of food and agriculture 85: 2354-2361 (2005).
Haslam, E. Natural polyphenois (vegetable tannins) as drugs: possible modes of action. J. of Natural Products 59: 205-215 (1996).
Hasson, et al. Protein cross-linking by peroxidase: possible mechanism for sclerotization of insect cuticle. Archives of Insect Biochemistry and Physiology 1 page (abstract) (Dec. 16, 1986).
Heber, D. Multitargeted therapy of cancer by ellagitannins. Cancer Letters 269: 262-268. (2008).
Heumann, et al. Initial responses to endotoxins and Gram-negative bacteria. Int J Clin Chem 323: 59-72 (2002).
Ho, et al. Antioxidative effect of polyphenoi extract prepared from various chinese teas. Prev. Med. 21(4): 1 page (abstract) (Jul. 1992).
Hughes. First-line treatment in acute non-dysenteric diarrhea: clinical comparison of loperamide oxide, loperamide and placebo. BJCP 49(4): 181-185 (1995).
Hussein, et al. In vitro study of the effects of green, red, and black tea and coffee extracts on the mammalian intestinal smooth muscle motility (contractions &relaxation). J. of Basrah Researches (Science) 36(4): 55-59 (Aug. 2010).
Hyslop, et al. Hydrogen peroxide as a potent bacteriostatic antibiotic: implactions for the host. Free Radical Biology & Medicine 19(1): 31-37 (1995).
Ishiguro, et al. Effects of conjugated linoleic acid on anaphylaxis and allergic pruritus. Biol. Pharm. Bull., 25(12): 1655-1657 (Dec. 2002).
Ishikawa, et al. Effect of tea flavonoid supplementatation on the susceptibility of low-density lipoprotein to oxidative modification, abstract, Am J Clin Nutr. 66(2): 1 page (Aug. 1997).
Ismail, et al. Pomegrante peel and fruit extracts: a review of potential anti-imflammatory and anti-infective effects. J Ethnopharmacol 143(2): 397-405 (2012).
Izzi, V., et al. The effects of dietary flavonoids on the regulation of redox inflammatory networks. Front biosci 17: 2396-2418 (2012).
Jailwala, J., et al. Pharmacologic treatment of irritable bowel syndrome: a systematic review of randomized, controlled trials. Ann Intern Med 133(2): 136-47 (2000).
Jan,; Online, URLhttps://forums.prohealth.com/forums/index.php?threads/severe-gastric-anyone-cant-do-meds.93998/.Internet posting date Jan. 23, 2004.
Jean-Gilles, D. Anti-inflammatory and cartilage protective effects of punicalagin, a major hydrolyzable tannin isolated from pomegran-

(56) References Cited

OTHER PUBLICATIONS ate, and a crude red raspberry extract in vitro and in vivo. search. proquest.con//docview/963705710 Abstract (2011).
Jiménez, A., et al. Evidence for the presence of the ascorbate-glutathione cycle in mitochondria and peroxisomes of pea leaves. Plant Physiol. 114(1): 275-284 (1997).
Jiménez, A., et al. Ascorbate-Glutathione cycle in mitochondria and peroxisomes of pea leaves: changes induced by leaf senescence. Phyton 37: 101-108 (1997).
Kabara, J.J., et al. Fatty acids and derivatives as antimicrobial agents. Antimicrobial Agents and Chemotherapy, 2(1): 23-28 (Jul. 1972).
Kahn, Khazaain-al-advia. vol. II (20th century AD), Nadeem Yunas Printer/Sheikh Mohd Basheer & Sons, Lahore, p. 611 (1911).
Kamen et al. Stimulation by dinitrophenol of formation of melanin-like substance from tyrosine by rat liver homogenates. The Journal of Biological Chemistry. 735-744 downloaded from www.jbc.org, (Oct. 31, 2008).
Kaplan, et al. Loperamide-simethicone vs loperamide alone, simethicone alone, and placebo in the treatment of acute diarrhea with gas-related abdominal discomfort. Arch Fam med 8: 243-248 (1999).
Kashiwada et al. Antitumor agents, 129. Tannins and related compounds as selective cytotoxic agents, abstract, J Nat Prod. 55(8): 1 page (Aug. 1992).
Khan, S.S., et al. Anthelmintic potential of crude extract of *Camellia sinensis* (green tea). Intern. Research Journ. Pharm. 4(3): 94-96 (2013).
Khennouf, et al. Effect of tannins from *Quercus suber* and *Quercus coccifera* leaves on ethanol-induced gastric lesions in mice. Journ. Agricul. Food Chem. 51(5): 1469-1473 (2003).
Khennouf, S., et al. Effect of some phenolic compounds and Quercus tannins on lipid peroxidation. World Appl. Sci. 8(9): 1144-1149 (2010).
Kilic et al. Fatty acid compositions of seed oils of three turkish salvia species and biological activities. Chemistry of Natural Compounds Springer Science+Business Media Inc. 41(3): 276-279 (Jan. 2005).
Kim et al. Effect of glutathione, catechin and epicatechin on the survival of *Drosophilia melanogaster* under paraquat treatment. Biosci. Biotechnol Biochem 61(2): 1 page abstract (Feb. 1997).
Kim et al. Research note: antimicrobial effect of water-soluble muscadine seed extracts on *Escherichia coli* 0157:h7. Journal of Food Protection, 71(7): 1 page abstract (Jul. 2008).
Kim et al. Measurement of superoxide dismutase-like activity of natural antioxidants. Viosci Biotechnol Biochem 59(5): 1 page (Abstract) (May 1995).
Kirsch, M., et al. Metastasis and angiogenesis. Cancer Treat. Res. 4: 285-304.
Koloski N.A., et al. The brain-gut pathway in functional gastrointestinal disorders is bidirectional. A 12- year prospective population-based study. Gut 61(9): 1284-1290. (2012).
Kolodziej, H., et al. Antileishmanial activity and immune modulatory effects of tannins and related compounds on leishmania parasitised raw 264.7 cells. Phytochemistry 66(17): 2056-2071 (2005).
Kostyuk, et al. The promose of plant polyphenois as the golden standard skin anti-inflammatory agents. Curr drug metab 11(15): 414-424 (2010).
Krab-Husken, L. Production of catechols, microbiology and technology, Thesis Wageningen University, The Netherlands, ISBN 90-5808-678-X, pp. 9-144 (Jan. 2002).
Ku, C.S., et al. Antioxidant activities of ethanol extracts from seeds in fresh Bokbunja (*Rubus coreanus* Miq.) and wine processing waste. Bioresource Tech. 99: 4503-4509 (2008).
Kuboe, et al. Quinone cross-linked polysaccharide hybrid fiber. Biomacromolecules, 5(2): 348-357 (2004).
Labieniec, M. et al. Study of interactions between phenolic compounds and $h_2o_2$ or $cu(ii)$ ions in b14 chinese hamster cells. Cell Biology Int'l, 30, pp. 761-768 (2006).
Labieniec, M. et al. Response of digestive gland cells of freshwater mussel unio tumidus to phenolic compound exposure in vivo. Cell Biology International. 31(7): 683-690 (2007).
Lady Bird Johnson Wildflower Center; 'Ask Mr. Smarty Plants'; Online, URLhttps://www.wildflower.org/expert/show.php?id=2947 Sep. 21, 2008, 2 pages.
Lagrimini, L.M. Wound-Induced deposition of polyphenols in transgenic plants overexpressing peroxidase. Plant Physiol, 96, pp. 577-583 (1991).
Laine et al. Risk factors for post-weaning diarrhea on piglet producing farms in Finland. Acta Vet Scand 50: 21-32 (2008).
Lalles, et al. Nutritional management of gut health in pigs around weaning. Proc Nutr soc 66: 260-268 (2007).
Lamb, C., et al. The oxidative burst in plant disease resistance. Annu Rev Plant Physiol Mol Bio, 48: 251-275 (1997).
Landolt, R., et al. Glyoxysome-like Microbodies in Senescent Spinach Leaves, PlantSci. 72(2): 159-163 (1990).
Lane, B.G., Oxalate oxidases and differentiating surface structure in wheat: germins. Biochem J 349: 309-321 (2000).
Lee et al. Antimicrobial synergistic effect of linolenic acid and monoglyceride against bacillus cereus and *Staphylococcus*. Journal of Agricultural and Food Chemistry 50: 2193-2199 (Jan. 2002).
Lewis, et al. Stool form scale as a useful guide to intestinal transit time. Scand j gastroenterol 32(9): 920-924 (1997).
Leshem, Y.Y. Plant senescence processes and free radicals. Free Radical Biol. Med. 5(1): 39-49 (1988).
Li, J., et al. Hydrogen peroxide and ferulic acid-mediated oxidative cross-linking of casein catalyzed by horseradish peroxidase and the impacts on emulsifying property and microstructure of acidified gel. African Journal of Biotechnology, 8(24): 6993-6999 (2009).
Li, W-Z., et al. Stabilizing the bactericidal activity of hydrogen peroxide: a brandnew function of certain chinese herbs. Chin J Integr Med, 6 pages (Dec. 3, 2012).
Liebregts T., et al. Immune activation in patents with irritable syndrome. Gastroenterology 132(3): 913-920 (2007).
Lin, C.C., et al. Hydrogen Peroxide level and nacl-inhibited root growth of rice seedlings. Plant and Soil, 230: 135-143 (2001).
Lin, et al. Tannin inhibitas HIV-1 entry by targeting gp41. Acta Pharmacol Sin. 25(2): 213-218 (Feb. 2004).
Longstreth G. et al. Functional bowel disorders. Gastroenterology 130: 1480-1491. (2006).
López-Huertas, E. et al. Superoxide generation in plant peroxisomal membranes: characterization of redox proteins involved. Biochem. Soc. Trans, 24: 195S (1996).
López-Huertas, E. et al. Superoxide radical generation in peroxisomal membranes: evidence for the participation of the 18-kda integral membrane polypeptide. Free Radical Res, 26(6): 497-506 (1997).
Lopez-Huertas, E. et al. Stress induces peroxisome biogenesis genes. The EMBO Journal 19(24): 6770-6777 (2000).
Lotito et al. Catechins delay lipid oxidation and α-tocopherol and β-carotene depletion following ascorbate depletion in human plasma. Society for Experimental Biology and Medicine 32-38 (Apr. 2000).
Low, P.S. et al. The oxidative burst in plant defense: function and signal transduction. Physiologia Plantarum 96(3): 533-542 (1996).
Lu. L., et al. Tannin Inhibits HIV_1 entry by targeting gp41. Acta Pharmacol Sin 25(2): 213-218 (Feb. 2004).
Luster, D.G. et al. Orientation of electron transport activities in the membrane of intact glyoxysomes isolated from castor bean endosperm. Plant Physiol 85: 796-800 (1987).
Macphillamy H.B. Drugs from plants. Plant Science Bulletin 9(2): 1-15 (Apr. 1963).
Maffei, et al. Relevance of apple consumption for protection against oxidative damage induced by hydrogen peroxide in human lymphocytes. The British Journal of Nutrition, Cambridge 97(5): 921-928 (May 2007).
Manzanilla, et al. Effect of plant extracts and formic acid on the intestinal equilibrium of early-weaned pigs. J Anim Soc 82: 3210-3218 (2004).
Matile, P. et al. Chlorophyll breakdown in senescent leaves. Plant Physiol., 112(4): pp. 1403-1409 (1996).

(56) References Cited

OTHER PUBLICATIONS

Matsumoto et al. Inhibitory effects of tea catechins, black tea extract and oolong tea extract on hepatocarcinogenesis in rat. Jpn. J. Cancer Res. 87(10): 1034-8 [1page abstract] ( Oct. 1996).

Mattiello, T. et al. Effects of pomegranate juice and extract polyphenols on platelet function. J med food 12(2): (2009).

McLean, J. C., et al. A simple screening protocol for the identification of quorum signal antagonists. J. Microbiological Methods 58: 351-360 (2004).

McNally, J.S., et al. Regulation of xanthine oxidoreductase protein expression by hydrogen peroxide and calcium. Arteriosclerosis, Thrombosis, and Vascular Biology 25: 1623-1628 (2005).

Mizobutsi, G.P., et al. Effect of pH and temperature on peroxidase and polyphenoloxidase activities of litchi pericarp. Sci. Agric. (Piracicaba, Braz.) 67(2): 213-217 (Mar./Apr. 2010).

Mohammad.Bin Zakariyya Al-Razi; Kitaab-al-Haawi-fil-Tibb, vol. IX ($9^{th}$ century A.D.), Dayerah-al-Ma'aarif Usmania, Hyderabad, (First Edition) p. 194 (1960).

Mohammad.Bin Zakariyya Al-Razi; Kitaab-al-Haawi-fil-Tibb, vol. XX ($9^{th}$ century A.D.), Dayerah-al-Ma'aarif Usmania, Hyderabad, (First Edition) p. 226 (1967).

Mohammadi, M. et al. Changes in peroxidase and polyphenol activity in susceptible and resistant wheat heads inoculated with fusarium granminearum and induced resistance. Plant Science (162): 491-498 (2002).

Mole, S. et al. Allelochemicals: Role in Agriculture and Forestry. Washington D.C., A.C.S. 572-587 (1987).

Morris et al. Affinity precipitation of proteins by polyligands, http://www.ncbi.nlm.nih.gov/pubmed/18601281. Biotechnol Bioeng. 41(10): 1 page. (Apr. 25, 1993).

Mugabe, C., et al. Mechanism of enhanced actibvity of liposoome-entrapped aminoglycosides against resistant strains of pseudomonas aeruginosa. Antimicrob Agents and Chemotherapy 50: 2016-2022 (2006).

Nanjo et al. Scavenging effects of tea catechins and their driviatives on 1, 1-diphenyl-2-picrythydrazyl radical. (Abstract) free Radic. Bioi. Med. 21(6): 1page (Jan. 1996).

Narayanan, B., et al. p53/p21 (WAF1/CIP1) Expression and its possible role in g1 arrest and apoptosis in ellagic acid treated cancer cells. Cancer Letters 136: 215-221 (1999).

Naz, S., et al. Antibacterial activity directed isolation of compounds from Punica granatum. 27(8): Journal of food science 72(9): 341-345 (2007). See cite No. 125 reference No. 13 on translated office action for JP2011-553012 for relevance.

Nguyen, D. What Are the Two Ways to Inhibit Enzyme Activity? http://classroom.synonym.com/two-ways-inhibit-enzyme-activity-11541.html (uploaded May 9, 2016).

Nishimura, M., et al. Leaf peroxisomes are directly transformed to glyoxysomes during senescence of pumpkin cotyledons. Protoplasma 175(3-4): 131-137 (1993).

Nonaka, G-I., et al. Anti-AIDS Agents, 2: inhibitory effects of tannins on hiv reverse transcriptase and hiv replication in h9 lymphocyte cells. J. Natl. Prod. 53(3): 587-595 (1990).

Obermeier et al. Effects of Bioflavonoids on Hepatic P450 Activities. Xenobiotica 25(6): abstract 1 page (Jun. 1995).

Omega-3 Fatty Acids. University of Maryland Medical Center, http://www.umm.edulaltmedlarticles/omeza-3-000316.htm [accessed Feb. 12, 2010].

Opal, SM. Endotoxins and other sepsis triggers. Contrib Nephrol 167: 14-24 (2010).

Orozco-Cardenas, M., et al. Hydrogen peroxide is generated systematically in plant leaves by wounding and systemin via the octadecanoid pathway. Proc. Natl. Acad. Sci. USA, 96: 6553-6557 (May 1999).

Page, JG, et al. Treatment of the irritable bowel syndrome with Bentyl (dicyclomine hydrochloride). J Clin Gastroenterol 3(2): 153-156 (1981).

Palombo, E. A. Phytochemicals from traditional medicinal plants used in the treatment of diarrhea: Modes of action and effects on intestinal function. Pyhtotherapy research 20: 717-724 (2006).

Park, et al. Rapid cessation of acute diarrhea in pediatric patents using a novel plant extract. . Poster presentation at the annual meeting of North America Society of Pediatric Gastronterology, Hepatology and Nutrition, Oct. 2012. Cumulative of poster at Park, K.T. et al. Ann Mtg North Soc Ped Gastro Hepato and Nutrition (Oct. 2012) online http://lifedropsinternation.com/solution (downloaded Feb. 11, 2015).

Parrish, JR et al. Effects of conjugated linoleic acid (cla) on swine performance and body composition. Jan. 1998/1997 Swine Research Report, Iowa State University, AS-638, 187-190 (1998).

Pastori, G.M., et al. An Activated-oxygen-mediated role for peroxisomes in the mechanism of senescence of pisum sativum. Planta 193(3): 385-391 (1994).

Pastori, G.M., et al. Activated oxygen species and superoxide dismutase activity in peroxisomes from senescent pea leaves. Proc R Soc Edinb Sect B Biol. 102B, 505-509 (1994).

Pastori, G.M., et al. Natural senescence of pea leaves: an activated oxygen-mediated function for peroxisomes. Plant Physiol., 113(2): 411-418 (1997).

Perez, Y.Y., et al. Effect of a Polyphenol-Rich Extract from Aloe vera Gel on Experimentally Induced Insulin Resistance in Mice. Am. J. of Chinese Med. XP055279252. p. 1037-1046 (2007).

Pierce Biotechnology, Inc. Protein stability and storage. TR0043.1 (2005).

Pistelli, L., et al. Glyoxylate cycle enzyme activities are induced in senescent pumpkin fruits. Plant Sci. 119(1-2); 23-29 (1996).

Poyrazoglu, E., et al. Organic acids and phenolic compounds in a pomegranates (*Punica granatum* I.) grown in turkey. J Food Comp Analysis 15: 567-575 (2002).

Preuss, H.G., et al. Minimum inhibitory concentrations of herbal essential oils and monolaurin for gram-positive and gram-negative bacteria. Molecular and Cellular Biochemistry, 272, pp. 29-34 Jan. 2005.

"Prevention" in Glossary of Medical Education Terms: Parts 1-7. Wojtczak, A., Ed. Medical Teacher. vol. 24, Nos. 2-6 and vol. 25, No. 1&2 (2002).

Pritchett,S., et al. Accidental ingestion of 35% hydrogen peroxide. Can J. Gastroenterol 21(10): 665-667 (2007).

Prottey et al. The mode of action of ethyt lactate as a treatment for acne. British Journal of Dermatology 110(4): (Jul. 29, 2006).

Pryor, M.G.M. On the hardening of the ootheca of blatta orientalis. Soc Lond Ser B, 128: 378-393 (1940).

PubChem, Tannic acid. Datasheet(online). NCBI,NIH. Mofify date: Dec. 17, 2016: (Copyright NCBI. NLM.NIH. Bethseda, MD: https://pubchem.ncbl.nlm.nih.gov/compound/16129778: p. 1: retrieved onDec. 23, 2016.

Quideau, S., et al. Main structural and stereochemical aspects of the antiherpetic activity of nonahydroxyterphenoyl-containing c-glycosidic ellagitannins. Chemistry and Biodiversity 1(2): 247-258 (2004).

Quideau, S., et al. Plant polyphenols: chemical properties, biological activities, and synthesis. Angew Chem Int Ed 50: 586-621 (2011).

Raphael, E. Phytochemical constituents of some leaves extract of Aloe vera and Azadirachta indica plant species. Global Adv. Res. J. of Env. Sci. And Toxicology. XP055279268 p. 14-17 (2012).

Raskin, et al. Can an apple a day keep the doctor away? Current Pharmaceutical Design 10: 3419-3429 (2004).

Rasheed K. J. Detection of the klebsiella pneumonia carbapenemase type 2 carbapenem-hydrolyzing enzyme in clinical isolates of citrobacter freundii and k. oxytoca carring a common plasmid. Journal of clinical microbiology 46(6): 2006-2069 (2008).

Ratnakara, Complied by Naginadasa Chaganalala Saha, Translated by Gopinath Gupta, vol. V: B. Jain Publishers, New Delhi, Edn. $2^{nd}$ Reprint, Aug. 1999.[This book contains back references from 1000 B.C. to 20 th century] p. 736 (1999).

Ray, H., et al. Transformation of potato with cucumber peroxidase: expression and disease response. Physiological and Molecular Plant Pathology 53: 93-103 (1998).

Robertson, J.A. et al. Peroxidase-mediated oxidative cross-linking and its potential to modify mechanical properties in water-soluble polysaccharide extracts and cereal grain residues. J Agric Food Chem 56(5): 1 page abstract (2008).

(56) References Cited

OTHER PUBLICATIONS

Rodrigues, A. C., et al. Anti-quorum sensing activity of phenolic extract from *Eugenia brasiliensis* (Brazilian cherry). Food Sci. technol, Caminas 36(2): 337-343 (2006).
Roginsky et al. Oxidation of tea extracts and tea catechins by molecular oxygen. Journal of Agricultural Food Chemistry 52(II) 1 page abstract (Apr. 30, 2005).
Romier, B., et al. Dietary polyphenols can modulate the intestinal inflammatory response. Nutr rev 67(7): 368-378 (2009).
Rosca-Casian. O et al, Antifungal activity of Aloe vera leaves, Filoterapia 78: 219-222 (2007).
Rucker et al. Copper, lysyl oxidase, and extracellular matrix protein cross-linking. The American Journal of Clinical Nutrition, '67(suppl.). 996S-1002S (Jan. 1998).
Sachinidis et al. Are catechins natural tyrosine kinase inhibitors? Drug News & Perspectives 15(7): 432, ISSN 0214-0934, 1 page Jan. (2002).
Sarmiento, et al. Postweaning diarrhea in swine. Am J Vet Res 49: 1154-1159 (1988).
Sasaki, et al. Ecabet sodium prevents the delay of wound repair in intestinal epithelial cells induced by hydrogen peroxide. J. Gastroenterol 40: 474-482 (2005).
Sato, et al. Ammonia, hydrogen peroxide, and monochloramine retard gastric epithelial restoration in rabbit cultured cell model. Digestive Diseases and Sciences 44(12): 2429-2434. (Dec. 1, 1999).
Schiller L.R. Definitions, pathophysiology, and evaluation of chronic diarrhea. Best pract res din gastroenterol 26(5): 551-562. (2012).
Schopfer, P. et al. Realease of reactive oxgen intermediates (Superoxide radicals, hydrogen peroxide, and hydroxyl radicals) and peroxidase in germinating radish seeds controlled by light, gibberellin, and abscisic acid. Plant Physiology 125: 1591-1602 (Apr. 2001).
Schweikert et al. Scission of polisaccharides by peroxidase-generated hydroxyl radicals. Phytochemistry 53(5): 2 pages (Mar. 1, 2000).
Scott, et al. Evaluation of the antioxidant actions of ferulic acid and catechins. Free Radic Res Commun 19(4): 1 page abstract (Jan. 1993).
Sebedio, J-L, et al. Vegetable oil products. Advances in conjugated linoleic acid research. 2, Urbana, IL, 2 pages (Jan. 2003).
Seeram, N.P., et al. Bioavailability of ellagic acid in human plasma after consumption of ellagitannins from pomegranate (*Punica granatum* L.) juice. Clinica Chimica Acta 348: 63-68 (2004).
Selinheimo, Tyrosinase and laccase as novel crosslinking tools for food Biopolymers, Online URL: http:/lib.tkk.fi/Diss/2008/isbn9789513871185/index.html, Page maintained by: diss@tkk, fi, 5 pages, [accessed Feb. 2, 2010].
Shimizu, M. Modulation of intestinal functions by food substances. Nahrung 43: 154-158 (1999).
Sidhu, K., et al. Prevention and cure of Digestive Disorders Through the Use of Medicinal Plants. J. Hum Ecol. 21(2): 113-116 (2007).
Smart, C.M. Gene expression during leaf senescence. New Phytol 126(3): 419-448 (1994).
Smkaradajisastripade, Aryabhisaka-Gujarati Edited (Hindustana No Vaidyaraja) Translation by Harikrishna Bhagwan Lal Vyas: Sastu Sahitya Vardhaka Karyalaya, Bhadra, Ahmedabad, Edn. 12$^{th}$, p. 92 (1957).
Spreeuwenberg, et al. Small intestine epithelial barrier function is compromised in pigs with low feed intake at weaning. J Nutr 131: 1520-1527 (2004).
Stachowicz, J.J., et al. Reducing predation through chemically mediated camouflage: indirect effects of plant defenses on herbivores. Ecology, 80(2): 495-509 (1999).
Stahmann, M.A., et al. Cross linking of proteins in vitro by peroxidase. Biopolymers 16(6): 1307-1318 (1997).
Stapleton et al. Potentiation of catechin gallate-mediated sensitization of *Staphylococcus aureus* to oxacillin by nongalloylated catechins. Antimicrobial Agents and Chemotherapy. 752-755 (Feb. 2006).
Stark, D., et al., Irritable bowel syndrome: a review of the role of intestinal protozoa and the importance of their dectection and diagnosis. Intl J Parasitology, 37, 11-20 (2007).
Steele, et al. Chemopreventive efficacy of black and green tea extracts in vitro assays, meeting. abstract, Proc Annu Meet Am Assoc Cancer Res, 37, 1 page (Jan. 1996).
Sugumaran, M., Comparative biochemistry of eumelanogenesis and the protective roles of phenoloidase and melamin in insects. Pigment Cell Res, 15(1): 2-9 (2002).
Taguri, T., et al. Antimicrobial activity of 10 different plant polyphenols against bacteria causing food-borne disease. Biol. Pharm. Bull. 27(12): 1965-1969 (2004).
Tanimura, S., et al. Suppression of tumor cell invasiveness by hydrolyzable tannins (plant polyphenols) via the inhibition of matrix metalloproteinase-2/-9 activity. Biochemical and Biophysical Research Communications, 330, 1306-1313 (2005).
Taormina, P.J. et al. Inhibitory Activity of honey against foodborne pathogens as influenced by the presence of of hydrogen peroxide and level of antioxidant power, International Journal of Food Microbiology: 69: 217-225: (2001).
Taras, et al. Performance, diarrhea incidence, and occurrence of *Escherichia coli* virulence genes during long-term administration of a probiotic Enterococcus faecium strain to sows and piglets. J Anim Sci 84: 608-616 (2006).
Terao et al. Protective effect of epicatechin, epicatechin gallate, and quercetin on lipid peroxidation in phospholipid bilayers, abstract; Arch Biochem Biophys, 308(1): 1 page. Jan. 1994.
Thompson, J.E., et al. Tansley review No. 8. The role of free radicals in senescence and wounding. New Phytol 105: 317-344 (1987).
Tomisato, et al. Maturation associated increase in sensitivity of cultured guinea pig gastric pit cells to hydrogen peroxide. Digestive Diseases and Sciences, New York, September. 47(9): 212-2132 (2002).
Taguri, et al. Antimicrobial activity of 10 different plant polyphenois against bacteria causing food-borne disease. Biol. Pharm. Bull. 27(12): 1965-1969 (2004).
Trinkley, K.E., et al. Treatment of irritable bowel syndrome. J. of Clinical Pharmacy and Therapeutics 36:275-282 (2011).
Tsao, R. Chemistry and biochemistry of dietary polyphenols. Nutrients 2: 1231-1246.
USP Technologies. Hydrogen Peroxide (H2O2) Safety and Handling Guidelines. httpi//www.h2o2.com/technical-librarv/defaylt. aspx?pid=88 p. 1-2 (2016).
Uyama et al. Enzymatic synthesis and properties of polymers from polyphenols, advances in polymer science, 194, ISSN 0065-3195, 1 page (Jan. 2006).
Valcic et al. inhibitory effect of six green tea catechins and caffeine on the growth of four selected human tumor cell lines. Anticancer Drugs. 7(4): 1 page abstract (Jun. 1996).
Van Breusegem, F., et al. The role of active oxygen species in plant signal transduction. Plant Science 161:405-414 (2001).
Van Den Bosch, H., et al. Biochemistry of Peroxisomes. Annu. Rev. Biochem. 61: 157-197 (1992).
Vangasena, Commentator Shaligram Vaisya, Edited Shankar Lalji Jain: Khemraj Shrikrishna Das Prakashan, Bombay, Edn. p. 1046 (1996).
Van Gerlder, C.W.G., et al. Sequence and structural features of plant and fungal tyrosinases. Phytochemistry 45(7): 1309-1323 (1997).
Varghese et al. Effect of asoka on the intracellular glutathione levels and skin tumor promotion in mice. Cancer Letter 69(1): 1 page abstract (Apr. 15, 1993).
Vauzour, D., et al. Polyphenois and human health: prevention of disease and mechanisms of action. Nutrients 2(11): 1106-1131 (2010).
Vermerris, W., et al., Phenolic compound biochemistry, Springer, 13 pages (2008).
Vetel, et al.Comparision of raceadotril and loperamide in adults with acute diarrhea. Aliment Pharmacol Ther 13(6): 21-26 (1999).
Wang, H.H., et al. A blind, randomized comparison of raceadotril and loperamide for stopping acute diarrhea in adults. World J Gastroenterol 11(10): 1540-1543 (2005).

(56) References Cited

OTHER PUBLICATIONS

Wang, S.X., et al. A crosslinked cofactor in lysyl oxidase: Redox function for amino acid side chains. Science 273(5278): 1078-1084. (1996).

Webster's Dictionary: Prophylactic: Online, URL<http://www.merriam-webster.com/dictionary/prophylactic> accessed Mar. 6, 2014, 3 pages.

Weiss, et al. Review: Conjugated linoleic acid: historical context and implications1. Professional Animal Scientist, 29 pages (Apr. 2004).

Wiechers, J.W., Nutraceuticals and nanoparticles, cosmetics & toiletries magazine, CosmeticsAndToiletries.com, http://www.cosmeticsandtoiletries.com/research/techtransfer/9431641.html?page=4.

Willekens, H., et al. Catalase is a sink for $h_2o_2$ and is indispensable for stress defense in $c_3$ plants. The EMBO Journal 16(16): 4806-4816 (1997).

Wikipedia, Catechin. http://en.wikipedia.org/wiki/Catechin (uploaded Jan. 5, 2011).

Wikipedia, Tannin, http://en.wikipedia.org/wikilTannin, 35 pages, This page was last modified on Jan. 30, 2010.

Williams, D.G. The Many Benefits of Hydrogen Peroxide. Internet achive date: 2003-0803 Retrieved from: https://web.archive.org/web/20030803175601/http://educate-yourself.org/cancer/benefitsofhydrogenperozide17jul03.shtml>. (Jul. 22, 2017).

Woo, E. J., et al. Germin is a manganese containing homohexamer with oxalate oxidase and superoxide dismutase activities. Nature Structural Biology 7(11): 1036-1040. (2000).

World Health Organization. Aloe Vera Gel. WHO monographs on selected medicinal plants 1: p. 43-49 (1999).

Worthington Biochemical Corporation. Effects pf pH (Introduction to Enzymes) http://www.worthington-biochem.com/introbiochem/effectspH.html (uploaded May 9, 2016).

Wu, et al. A novel plantextract mix is capable of binding endotoxin. Poster presentation at international symposium on alternatives to antibiotics. Program to Alternatives to antibiotics (ATA). The world organization for animal health, Paris, France:77 (Sep. 25-28, 2012.).

Wu. Phytobiologics: Novel natural compounds for improving enteric health in nursing pigs. American association of swine veterinarians 207-210 (2013).

Wu-Yuan et al. Gallotannins inhibit growth, water-insoluble glucan synthesis, and aggregation of mutans streptococci. J Dent Res 67(1): 51-55 (Jan. 1988).

Yamaguchi, K., et al. A novel isoenzyme of ascorbate peroxidase localized on dlyoxysomal and leaf peroxisomal membranes in pumpkin, Plant Cell Physiol.,36(6): 1157-1162 (1995).

Yamamoto et al. Roles of catalase and hydrogen peroxide in green tea polyphenol-induced chemopreventive effects, Journal of Pharmacology and Experimental Therapeutics Fast forward, 32 Pages, DOI:10.1124/jpet.103.058891, JPET #58891 (2003).

Yamamoto et al. Studies on quinone cross-linking adhesion mechanism and preparation of antifouling surfaces toward the blue mussel, abstract, Journal of Marine Bitechnology, 5(2-3): 1 page (May 1997).

Yang, L-L., et al. Induction of apoptosis by hydrolyzable tannins from eugenia jambos I. on human leukemia cells, Cancer Letters 157: 65-75. (2000).

Yokozawa, T., et al. Effects of rhubarb tannins on renal function in rats with renal failure. Nippon Jinzo Gakkai Shi 35(1):13-8 1 page abstract (Jan. 1993).

Yoshino et al. Antioxidative effects of black tea theaflavins and thearubigin on lipid peroxidation of rat liver homogenates induced by tert-butyl hydroperoxid. Biot Pharm Bull 17(1): 1 page abstract. (Jan. 1994).

Youn H. J. et al. Screening of the anticoccidial effects of herb extracts against Eimeria tenella. Veterinary parasitology 96: 257-263 (2001).

Zhang, Y., et al. Absence of Pomegranate Ellagitannins in the Majority of Commercial Pomegranate Extracts: Implications for Standardization and Quality Control. J. Agri. Food Chem. 57:7395-7400 (2009).

Zhang et al. Inhibitory effects of jasmine green tea epicatechin isomers on free radical-induced lysis of red blood cells. Life Sci 61(4): 1 page abstract (Jan. 1997).

Zheng, C.J. et al. Fatty acid synthesis is a target for antibacterial activity of unsaturated fatty acids. FEBS Letters, 579: 5157-5162. (2005).

Ziya Al-Din Abdullah Ibn Al-Baitar: Al-Jaam'e—li-Mufradaat-al—Advica-wal—Aghzia, vol. 1 ($13^{th}$ century AD), Matba Amra, Cairo, Egypt,. p. 162 (1874 A.D).

Zhu et al. Antioxidant chemistry of green tea catechins: oxidation products of (−)-epigallocatechin gallate and (−)-with peroxidase. Wiley InterScience Journals: Journal of Food Lipids 7(4): 1 page (May 5, 2007).

The X-axis represents the time in hours, including a point at 7 days
The Y-axis represents the hydrogen peroxide concentration in ppm The X-axis represents the time in hours
The Y-axis represents the hydrogen peroxide concentration in ppm

METHODS OF TREATING A TREATMENT-RESISTANT GASTROINTESTINAL SPASM

CROSS-REFERENCE TO RELATED APPLICATIONS

This application is a continuation of U.S. application Ser. No. 15/199,075, which is a continuation of U.S. application Ser. No. 14/745,426, filed Jun. 20, 2015, now U.S. Pat. No. 9,408,869, which is a continuation of U.S. application Ser. No. 14/662,725, filed Mar. 19, 2015, now U.S. Pat. No. 9,089,596, which is a continuation of U.S. application Ser. No. 14/584,419, filed Dec. 29, 2014, now U.S. Pat. No. 9,023,895, which is a continuation of U.S. application Ser. No. 14/317,970, filed Jun. 27, 2014, now U.S. Pat. No. 8,946,304, which is a continuation of U.S. application Ser. No. 14/272,047, filed May 7, 2014, now U.S. Pat. No. 8,809,399, which is a continuation of U.S. application Ser. No. 14/222,605, filed Mar. 22, 2014, now U.S. Pat. No. 8,772,352, which is a continuation of U.S. application Ser. No. 14/173,079, filed Feb. 5, 2014, now U.S. Pat. No. 8,772,350, which is a continuation of U.S. application Ser. No. 14/142,895, filed Dec. 29, 2013, now U.S. Pat. No. 8,716,353, which is a continuation of U.S. application Ser. No. 13/726,180, filed Dec. 23, 2012, now U.S. Pat. No. 8,716,351, each of which is hereby incorporated herein by reference in its entirety.

BACKGROUND

Field of the Invention

The teachings provided herein relate to methods of treating a gastrointestinal spasms associated with chemotherapy or radiation therapy.

Description of Related Art

Antispasmodics can be used to prevent spasms of the stomach, intestine, uterus, or urinary bladder. Gastrointestinal spasms, for example, can be very painful. Abdominal pain and discomfort from cramping, bloating, forceful vomiting, and forceful defecation are often the result of spasmodic intestinal contractions. The problem is that there is no satisfactory treatment to relieve the pain and suffering that currently exists due to this problem. Spasms can also be treated using "anticholinergics" that counteract the effects of the neurohormone acetylcholine. The anticholingergics decrease both the movements of the stomach and intestine, and also the secretions of stomach acid and digestive enzymes. Problems with these drugs include dry mouth and dry eyes because of reduced salivation and tearing.

An example of an anticholinergic that is used to treat cramping is loperamide, an opioid-receptor agonist that slows peristalsis. As such, it is not directed to relieve cramping from spasms, per se. Moreover, loperamide crosses the blood-brain barrier and, although quickly removed from the CNS by P-glycoprotein, it can be addictive if taken with a drug that inhibits P-glycoprotein. Moreover, loperamide has several contraindications, such that it's not recommended for use with several conditions that can include gastrointestinal spasms. For example, it is not recommended for treatment with conditions containing organisms that cross the intestinal walls, such as such as *E. coli* O157:H7 or *salmonella*. And, ironically, although it is often administered to alleviate abdominal pain and cramping, its adverse effects can actually include abdominal pain and bloating, nausea, vomiting and constipation. In fact, loperamide has been labeled as (i) contraindicated in patients with abdominal pain in the absence of diarrhea; (ii) not recommended in children below 24 months of age; and (iii) not recommended as the primary therapy in patients with (a) acute dysentery, which is characterized by blood in stools and high fever; (b) acute ulcerative colitis; (c) bacterial enterocolitis caused by invasive organisms including *Salmonella, Shigella*, and *Campylobacter*; or, (d) pseudomembranous colitis associated with the use of broad-spectrum antibiotics. See, for example, http://dailymed.nlm.nih.gov/dailymed/archives/fdaDruglnfo.cfm?archiveid=41053, Lake Erie Medical DBA Quality Care Products LLC.

A condition of particular interest in the treatment of gastrointestinal spasms is irritable bowel syndrome (IBS), a condition afflicting an estimated 30 million people in the US and up to 700 million people worldwide. IBS is diagnosed from clinical symptoms that include abdmoninal pain, bloating, constipation, and diarrhea. Treatment options are based upon the predominant symptom, with diarrhea-predominant IBS receiving antidiarrheal agents, such as loperamide (IMMODIUM) and pain-predominant IBS patients receiving antispasmodic agents, such as dicyclomine HCL (BENTRYL) and hyoscyamine sulfate (LEVSIN). The condition is generally thought to be the result of spasmodic contractions of the intestines that interfere with normal peristalsis causing blockages that lead to bloating and constipation, cause hyperperistaltic activity leading to frequent need for defecation, or a combination. Problems with loperamide are discussed above. Dicyclomine has the problem of some people sweat less, allowing the body to overheat which can cause heat prostration (fever and heat stroke). As such, anyone taking this drug should try to avoid extreme heat. Moreover, dicyclomine can also cause drowsiness and blurred or double vision, such that people who take this drug should not drive, use machines, or do anything else that might be dangerous. Hyoscyamine can also be used but, unfortunately, both dicyclomine and hyoscyamine have general side effects and, for example, can worsen gastroesophageal reflux disease. Anticholinergics, generally speaking, are also known to cause difficulty in passing urine, and children and the elderly are at a higher risk of developing such side effects.

One of skill would appreciate having a method of treating spasms, particularly gastrointestinal spasms, without having to use systemic drugs that have shown to (i) provide slow relief, (ii) cause adverse side effects, (iii) limit activities, (iv) worsen existing gastrointestinal conditions, (v) be unrecommended in several gastrointestinal conditions that include gastrointestinal spasms, and (vi) be unrecommended in the absence of diarrhea.

SUMMARY

The teachings provided herein relate to methods of treating gastrointestinal spasms. The teachings include methods of treating gastrointestinal spasms without having to use systemic drugs that have shown to (i) provide slow relief, (ii) cause adverse side effects, (iii) limit activities, (iv) worsen existing gastrointestinal conditions, (v) be unrecommended in several gastrointestinal conditions that include gastrointestinal spasms, or (vi) be unrecommended in the absence of diarrhea.

In some embodiments, the teachings are directed to a method of treating a gastrointestinal spasm in a subject, the method comprising administering an effective amount of a composition to a subject having a gastrointestinal spasm, the composition having a polyphenol combined with a reactive oxygen species. And, in some embodiments, the composition can be produced from a process including combining a polyphenol with a reactive oxygen species; selecting a desired concentration for the composition; and, diluting the composition to the desired concentration for the administering. In these embodiments, the polyphenol can have a molecular weight ranging from about 170 Daltons to about 4000 Daltons; and, the composition can relieve a gastrointestinal spasm in the subject either (i) when compared to a second subject in a control group in which the composition was not administered or (ii) when compared to a historic baseline of the symptoms present in the subject. The measurement of relief from gastrointestinal spasms can be measured using any of a variety of parameters, in some embodiments. For example, the relief of the spasm can be measured using a response selected from the group consisting of a reduction in abdominal pain, a reduction in bloating, a reduction in forceful defecation, a reduction in forceful vomiting, a reduction in defecation urgency, a reduction in constipation, and/or a reduction in incontinence.

The polyphenol can comprise a single component, a mixture of components, or a whole extract of a plant tissue, in some embodiments. In some embodiments, the polyphenol comprises a tannin. In some embodiments, the polyphenol comprises a hydrolysable tannin, a condensed tannin, or a combination of a hydrolysable tannin and a condensed tannin. In some embodiments, the polyphenol can comprise a pseudotannin selected, for example, from the group consisting of gallic acid, which can be found in an extract of a rhubarb plant tissue, for example; flavan-3-ols or catechins, which can be found in an extract of acacia, catechu, cocoa, or guarana, for example; chlorogenic acid, which can be found in coffee, or mate; or, ipecacuanhic acid, which can be found in carapichea ipecacuanha, for example. As such, it should be appreciated that, in some embodiments, the polyphenol component can comprise a flavanol or a catechin. Moreover, the polyphenol can comprises gallic acid, epigallic acid, or a combination thereof, in some embodiments.

The reactive oxygen species can be any such species known to one of skill to have the ability to combine with the polyphenol as a composition for the uses taught herein. In some embodiments, the reactive oxygen species comprises hydrogen peroxide. And, in some embodiments, the hydrogen peroxide can be combined with the tannin at a tannin:peroxide weight ratio that ranges from about 1:1000 to about 10:1. In some embodiments, the weight ratio of the tannin:peroxide ranges from about 1:1 to about 1:50.

And, consistent with the above, one of skill will appreciate that the polyphenol can be combined with the reactive oxygen species as a component of a water or alcohol extract of a plant tissue. In some embodiments, the plant tissue can comprise a tannin or a pseudotannin.

One of skill reading the teachings that follow will appreciate that the concepts can extend into additional embodiments that go well-beyond a literal reading of the claims, the inventions recited by the claims, and the terms recited in the claims.

DETAILED DESCRIPTION

Figures 1A, 1B:
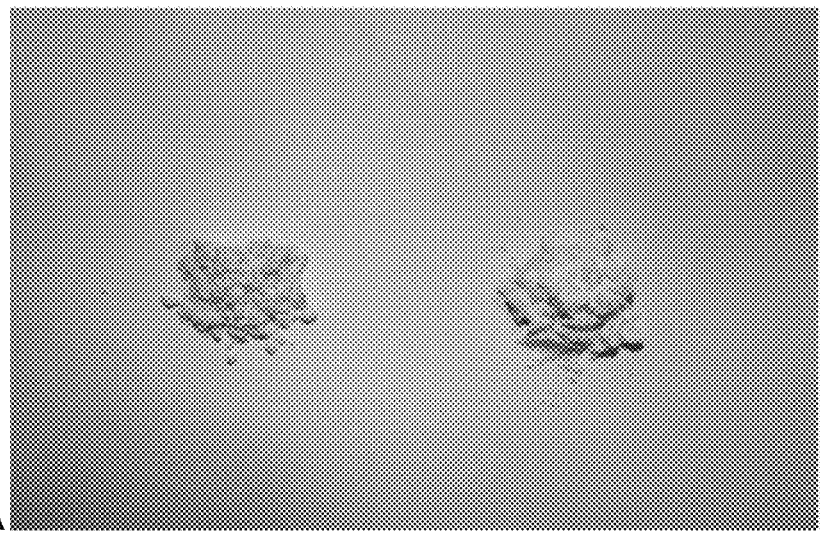
FIGS. 1A-1H are photographs of the dry forms of (A) gallic acid (a model polyphenol building block) bound to hydrogen peroxide; (B) gallic acid alone; (C) tannic acid (a model polyphenol) bound to hydrogen peroxide; (D) tannic acid alone; (E) pomegranate husk extract bound to hydrogen peroxide; (F) pomegranate husk extract alone; (G) green tea extract bound to hydrogen peroxide; and (H) green tea extract alone, according to some embodiments.
Figures 1C, 1D:
Figures 1E, 1F:
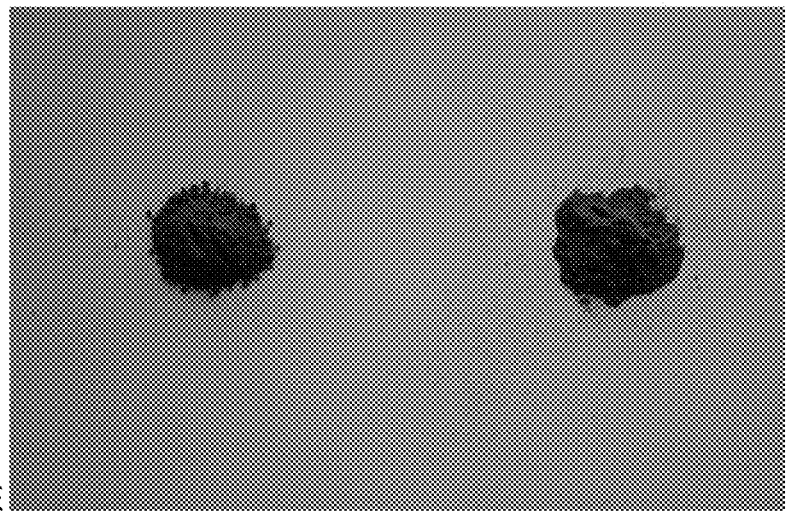
Figures 1G, 1H:
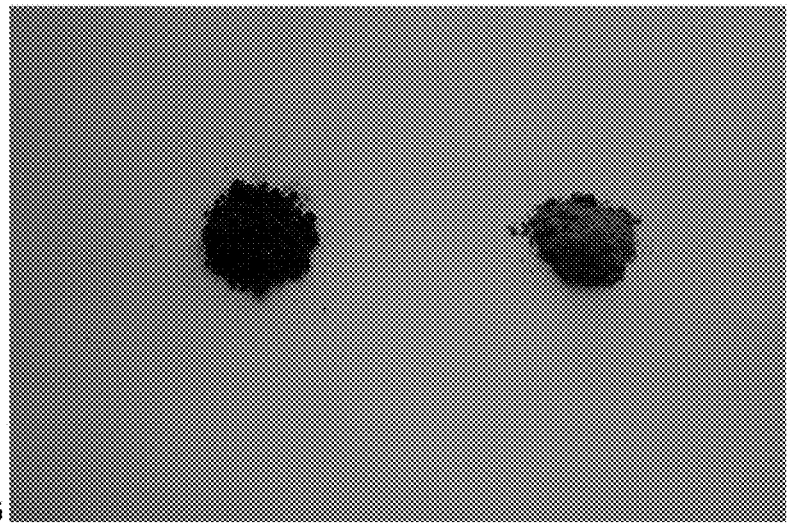

Methods of treating gastrointestinal spasms are provided herein. The methods include treating gastrointestinal spasms without having to use systemic drugs. Such systemic drugs have been reported to (i) provide slow relief, (ii) cause adverse side effects, (iii) limit activities, (iv) worsen existing gastrointestinal conditions, (v) be unrecommended in several gastrointestinal conditions that include gastrointestinal spasms, or (vi) be unrecommended in the absence of diarrhea.

In some embodiments, the method of treating a gastrointestinal spasm in a subject comprises administering an effective amount of a composition to a subject having a gastrointestinal spasm, the composition having a polyphenol combined with a reactive oxygen species. And, in some embodiments, the composition can be produced from a process including combining a polyphenol with a reactive oxygen species; selecting a desired concentration for the composition; and, diluting the composition to the desired concentration for the administering. In these embodiments, the polyphenol can have a molecular weight ranging from about 170 Daltons to about 4000 Daltons; and, the composition can relieve a gastrointestinal spasm in the subject either (i) when compared to a second subject in a control group in which the composition was not administered or (ii) when compared to a historic baseline of the symptoms present in the subject.

To provide a desired therapeutic relief, the compositions can be directed to act on tissues at a particular target site, which can be gastrointestinal tissue, in some embodiments. The term "target site" can be used to refer to a select location at which the composition acts to provide a therapeutic effect, or treatment as described herein. In some embodiments, the target site can be a tissue of any organ in which control of a spasm is desirable. Moreover, the target can include any site of action in which the phenolic compound can be site-activated by an oxidoreductase enzyme that is available at the site. The oxidoreductase enzyme can be produced endogeneously by a tissue at a target site, produced endogeneously by a microbe, introduced exogenously to the target site, include more than one enzyme, co-enzyme, catalyst, or cofactor, or a combination thereof. The measurement of relief from gastrointestinal spasms, for example, can be measured using any of a variety of parameters. For example, the relief of the spasm can be measured using a response selected from the group consisting of a reduction in abdominal pain, a reduction in bloating, a reduction in forceful defecation, a reduction in forceful vomiting, a reduction in defecation urgency, a reduction in constipation, and/or a reduction in incontinence.

Without intending to be bound by any theory or mechanism of action, the compositions taught herein can include phenolics, for example, polyphenols. The phenolic compounds taught herein are selected to combine with a reactive oxygen species to form a composition that is deliverable as a stable, or substantially stable, system. In some embodiments, the compositions can include a polyphenol component combined with hydrogen peroxide, a combination of components having an association that offers a stability and activity, both of which are offered by neither component alone. Such a composition can be delivered to a target site, for example, in a polar solution such as water or an alcohol. In some embodiments, at least a substantial amount of the hydrogen peroxide can remain bound, or otherwise associated with, and thus stable or substantially stable, with the phenolic compound. Moreover, in some embodiments, the composition contains no, or substantially no, unbound hydrogen peroxide. The teachings also include a pharmaceutical formulation comprising the compositions taught herein and a pharmaceutically acceptable excipient.

The terms "composition," "compound," "binding system," "binding pair," and "system" can be used interchangeably in some embodiments and, it should be appreciated that a "formulation" can comprise a composition, compound, binding system, binding pair, or system presented herein. Likewise, in some embodiments, the compositions taught herein can also be referred to as an "agent," a "bioactive agent," or a "supplement" whether alone, in a pharmaceutically acceptable composition or formulation, and whether in a liquid or dry form. Moreover, the term "bioactivity" can refer to a treatment that occurs through the use of the compositions provided herein. One of skill will appreciate that the term "bind," "binding," "bound," "attached," "connected," "chemically connected," "chemically attached," "combined," or "associated" can be used interchangeably, in some embodiments. Such terms, for example, can be used to refer to any association between the polyphenol and reactive oxygen species that has resulted in an increased stability and/or sustained activity of the composition or components in the compositions. For example, the terms can be used to describe a chemical bonding mechanism known to one of skill, such as covalent, ionic, dipole-dipole interactions, London dispersion forces, and hydrogen bonding, for example. In some embodiments, the compositions can comprise a phenolic compound sharing hydrogen bonds with a reactive oxygen species, for example, such as hydrogen peroxide. In some embodiments, the phenolic compound can comprise a polyphenol that covalently binds to an amino acid or polyol.

One of skill will appreciate that the compositions should remain stable, or at least substantially stable, until useful or activated, and this can relate to a measure of time. Such a measure of time can include a shelf life, or a time between creation of the composition and administration of the composition, or some combination thereof. In some embodiments, the composition is stable, or substantially stable, when usable as intended within a reasonable amount of time. In some embodiments, the composition should be usable within a reasonable time from the making of the composition to the administration of the composition and, in some embodiments, the composition should have a reasonable commercial shelf life. The composition can be considered as "stable" if it loses less than 10% of it's original oxidation potential, and this can be measured by comparing it's oxidation potential after making the composition to the time of administration, and this can include a reasonable shelf life, in some embodiments. In some embodiments, the composition can be considered as stable if it loses less than 5%, 3%, 2%, or 1% of it's original oxidation potential when comparing it's oxidation potential after making the composition to the time of administration, and this can include a reasonable shelf life, in some embodiments. The composition can be considered as "substantially stable" if it loses greater than about 10% of it's original oxidation potential, as long as the composition can perform it's intended use to a reasonable degree of efficacy. The loss can be measured, as above, by measured by comparing it's oxidation potential after making the composition to the time of administration, and this can include a reasonable shelf life, in some embodiments. In some embodiments, the composition can be considered as substantially stable if a reactive oxygen species loses greater than about 12%, about 15%, about 25%, about 35%, about 45%, about 50%, about 60%, or even about 70% of it's original oxidation potential. The loss may be measured by measured by comparing it's oxidation potential after making the composition to the time of administration, and this can include a reasonable shelf life, in some embodiments. The time to compare the oxidation potential for a measure of stability can range from about 30 minutes to about one hour, from about one hour to about 12 hours, from about 12 hours to about 1 day, from about one day to about one week, from about 1 week to about 1 month, from about 1 month to about 3 months, from about 1 month to a year, from 3 months to a year, from 3 months to 2 years, from 3 months to 3 years, greater than 3 months, greater than 6 months, greater than one year, or any time or range of times therein, stated in increments of one hour.

One of skill will appreciate that the phenolic compound used in the compositions can be any phenolic compound that functions consistent with the teachings provided herein, and there are at least several thousand such phenolic compounds known to those of skill that can be expected to function as desired. As such, the teachings provided herein can only include examples of the general concepts rather than a comprehensive listing of all possibilities and permutations of the systems that are enabled by the teachings.

The phenolic component can be a polyphenol, and the polyphenol can comprise a single component, a mixture of components, or a whole extract of a plant tissue, in some embodiments. In some embodiments, the polyphenol comprises a tannin. In some embodiments, the polyphenol comprises a hydrolysable tannin, a condensed tannin, or a combination of a hydrolysable tannin and a condensed tannin. In some embodiments, the polyphenol can comprise a pseudotannin selected, for example, from the group consisting of gallic acid, which can be found in an extract of a rhubarb plant tissue, for example; flavan-3-ols or catechins, which can be found in an extract of acacia, catechu, cocoa, or guarana, for example; chlorogenic acid, which can be found in coffee, or mate; or, ipecacuanhic acid, which can be found in carapichea ipecacuanha, for example. As such, it should be appreciated that, in some embodiments, the polyphenol component can comprise a flavanol or a catechin. Moreover, the polyphenol can comprises gallic acid, epigallic acid, or a combination thereof, in some embodiments.

In some embodiments, the phenolic compound has at least one aryl group, or arene moiety, and at least two polar aromatic groups, such as aromatic hydroxyl groups. In some embodiments, the polar aromatic groups can be, for example, hydroxyl, amine, amide, acyl, carboxy, or carbonyl. In some embodiments, the phenolic compound has at least two aryl groups, and at least two hydroxyl groups. In some embodiments, the phenolic compounds can be naturally occurring, such as from a plant or other natural product. And, in some embodiments, the phenolic compounds can be synthetically or semi-synthetically produced. The compounds can be simple monomers, oligomers, or polymers. The polymers can be in the class of polyphenols or polymeric phenols, where one of skill will understand that the general difference is typically that polyphenols generally do not have a repeating unit, whereas polymeric phenols do.

There are exceptions, however, such that groups of polyphenols and polymeric phenols can overlap. In most embodiments, the phenolic compound used in the binding system can be any phenolic compound taught herein, or any prodrugs, codrugs, metabolites, analogs, homologues, congeners, derivatives, salts, solvates, and combinations thereof.

In some embodiments, the phenolic compounds bind to hydrogen peroxide to form a binding pair and, in some embodiments, the binding pair remains stable, or substantial stable in water. In some embodiments, the binding pair remains stable, or substantial stable in an alcohol. And, in some embodiments, the binding pair remains stable, or substantial stable, in a polar solvent such as, for example, a saline solution, an aqueous emulsion, a hydrogel, and the like.

In some embodiments, the phenolic compounds are polyphenols having molecular weights ranging from about 170 to about 4000 Daltons, having from about 12 to about 16 phenolic hydroxyl groups, and having from about five to about seven aromatic rings, for every about 1000 Daltons in molecular weight. In some embodiments, the phenolic compounds function to precipitate alkaloids and proteins. In some embodiments, the phenolic compounds can bind to cellular receptors, amino acids, peptides, oligopeptides, polyols, saccharides, or combinations thereof. In some embodiments, the phenolic compounds have at least from about 1 to about 20 polyhydroxylated phenolic units and have at least moderate water solubility.

The term "solubility" can refer to a concentration of a solute in a solvent, for example, the phenolic compound in water. The concentration can be expressed by mass, for example, mg of the phenolic compound per kg of water at ambient temperature and pressure. This ratio of mg/kg can be used interchangeably with ppm, and ng/kg can be used interchangeably with ppb. In some embodiments, the solubility of the phenolic compound can be higher than about 500,000 ppm or less than about 1 ppm. In some embodiments, the solubility of the phenolic compound range from about 10 ppb to about 500,000 ppm, from about 100 ppb to about 250,000 ppm, from about 1 ppm to about 100,000 ppm, from about 10 ppm to about 50,000 ppm, from about 50 ppm to about 25,000 ppm, from about 100 ppm to about 10,000 ppm, from about 100 ppm to about 100,000 ppm, from about 200 ppm to about 100,000 ppm, from about 250 ppm to about 50,000 ppm, from about 500 ppm to about 25,000 ppm from about 250 ppm to about 10,000 ppm, or any range therein. In some embodiments, the solubility can range from about 1 g/L to about 10,000 g/L, from about 5 g/L to about 5000 g/L, from about 10 g/L to about 3000 g/L, from about 20 g/L to about 2000 g/L, from about 50 g/L to about 1000, g/L, from about 100 g/L to about 500 g/L, or any range therein. For purposes of the teachings provided herein, a compound can be considered to have a low solubility if the solubility is less than about 50 g/L, a moderate solubility if the solubility ranges from about 50 g/L to about 1000 g/L, and a high solubility if the solubility is above about 1000 g/L. In some embodiments, the phenolic compound can have a low solubility. In some embodiments, the phenolic compound can have a moderate solubility. And, in some embodiments, the phenolic compound can have a high solubility.

One of skill will appreciate that the phenolic compounds can still be useful at low solubilities in cases where the solubility is too low to form a true solution. In some embodiments the phenolic compounds can be ground into particles to form a colloidal mixture or suspension that will function consistent with the teachings provided herein. As such, liquid formulations include colloids and suspensions in some embodiments. The formulations can be a dispersed phase mixture in the form of colloidal aerosols, colloidal emulsions, colloidal foams, colloidal dispersions, or hydrosols. In some embodiments, the liquid formulation can include particles having sizes ranging, for example, from about 5 nm to about 200 nm, from about 5 nm to about 500 nm, from about 5 nm to about 750 nm, from about 50 nm to about 1 um. In some embodiments, the liquid formulations can be suspensions, in which the particle size range from about 1 um to about 10 um, from about 1 um to about 7 um, from about 1 um to about 5 um, or any range therein. In some embodiments, the liquid formulation can include particles having sizes ranging from about 1 nm to about 10 um.

The functionality of a phenolic compound in the teachings herein can, for at least the reason of solubility, depend on molecular weight, alone or in addition to other factors discussed herein such as, for example, extent of hydroxylation, presence and location of ketone or quinine groups, and the presence of other functional groups. In some embodiments, the molecular weights of the phenolic compounds can range from about 110 Daltons to about 40,000 Daltons. In some embodiments, the molecular weights of the phenolic compounds can range from about 200 Daltons to about 20,000 Daltons, from about 300 Daltons to about 30,000 Daltons, from about 400 Daltons to about 40,000 Daltons, from about 500 Daltons to about 10,000 Daltons, from about 1000 Daltons to about 5,000 Daltons, from about 170 Daltons to about 4000 Daltons, from about 350 Daltons to about 4,000 Daltons, from about 300 Daltons to about 3,000 Daltons, from about 110 Daltons to about 2,000 Daltons, from about 200 to about 5000 Daltons, or any range or molecular weight therein in increments of 10 Daltons.

In some embodiments, the ratio of aromatic rings to molecular weight of the phenolic compounds can range from about five to about seven aromatic rings for every about 1000 Daltons. In some embodiments, the ratio of aromatic rings to molecular weight of the phenolic compounds can range from about 2 to about 10 aromatic rings for every about 1000 Daltons, from about 3 to about 9 aromatic rings for every about 1000 Daltons, from about 4 to about 8 aromatic rings for every about 1000 Daltons, from about 5 to about 7 aromatic rings for every about 1000 Daltons, from about 1 to about 5 for every about 500 Daltons, from about 1 to about 4 for every about 500 Daltons, from about 1 to about 3 for every about 500 Daltons, from about 2 to about 4 for every about 500 Daltons, or any amount or range therein in increments of 1 ring.

One of skill will appreciate that, in some embodiments the phenolic compounds can have, or be synthesized or otherwise designed to contain functional groups that are capable of releasably bonding to a reactive oxygen species, in a stable or substantially stable form, until either consumed or released upon bioactivation at a target site. In some embodiments, a releasable bond can include any bond other than a covalent bond. In some embodiments, a releasable bond is a hydrogen bond. As such, the phenolic compounds should be capable of forming, for example, a hydrogen bond with a reactive oxygen species upon such bioactivation. In some embodiments, the phenolic compound shares hydrogen bonding with hydrogen peroxide and is released through a bioactivation that occurs when the binding pair comes into contact with an oxidoreductase enzyme or other reducing agent. In some embodiments, the phenolic compound can have functional groups that comprise acyl, amido, amino, carbonyl, carboxyl, hydroxyl, or peroxyl functionality. In some embodiments, the hydrogen bond between the reactive oxygen species and the phenolic compound can include any hydrogen donor and any hydrogen acceptor having an available lone pair of electrons. In some embodiments, the hydrogen acceptor can include, for example a N, O, or F atom, or a combination thereof. In some embodiments, the phenolic compound can have such a functionality, can be derivatized to have such a functionality, can be linked to another compound having such a functionality, can be placed in a carrier having such a functionality, or some combination thereof.

In some embodiments, phenolic compounds can include simple phenols, such as those containing 6 carbons, a C6 structure, and 1 phenolic cycle, such as the benzene alcohols, examples of which include phenol, benzene diols and it's isomers such as catechol, and the benzenetriols. In some embodiments, phenolic compounds can include phenolic acids and aldehydes, such as those containing 7 carbons, a C6-C1 structure, and 1 phenolic cycle, examples of which include gallic acid and salicylic acids. In some embodiments, phenolic compounds can include, for example, tyrosine derivatives, and phenylacetic acids, such as those containing 8 carbons, a C6-C2 structure, and 1 phenolic cycle, examples of which include 3-acetyl-6-methoxybenzaldehyde, tyrosol, and p-hydroxyphenylacetic acid. In some embodiments, phenolic compounds can include hydroxycinnamic acids, phenylpropenes, chromones, such as those containing 9 carbons, a C6-C3 structure, and 1 phenolic cycle, examples of which include caffeic acid, ferulic acids, myristicin, eugenol, umbelliferone, aesculetin, bergenon, and eugenin. In some embodiments, phenolic compounds can include naphthoquinones, such as those containing 10 carbons, a C6-C4 structure, and 1 phenolic cycle, examples of which include juglone and plumbagin. In some embodiments, phenolic compounds can include xanthonoids, such as those containing 13 carbons, a C6-C1-C6 structure, and 2 phenolic cycles, examples of which include mangiferin. In some embodiments, phenolic compounds can include stilbenoids, and anthraquinones, such as those containing 14 carbons, a C6-C2-C6 structure, and 2 phenolic cycles, examples of which include resveratrol and emodin. In some embodiments, phenolic compounds can include chalconoids, flavonoids, isoflavonoids, and neoflavonoids, such as those containing 15 carbons, a C6-C3-C6 structure, and 2 phenolic cycles, examples of which include quercetin, myricetin, luteolin, cyanidin, and genistein. In some embodiments, phenolic compounds can include lignans and neolignans, such as those containing 18 carbons, a C6-C3-C6 structure, and 2 phenolic cycles, examples of which include pinoresinol and eusiderin. In some embodiments, phenolic compounds can include biflavonoids, such as those containing 30 carbons, a $(C6-C3-C6)_2$ structure, and 4 phenolic cycles, examples of which include amentoflavone. In some embodiments, phenolic compounds can include polyphenols, polyphenolic proteins, lignins, and catechol melanins, such as those containing >30 carbons. In these embodiments, the phenolic compounds can have, for example, a $(C6-C3)_n$ structure, a $(C6)_n$ structure, a $(C6-C3-C6)_n$ structure, or some combination thereof, as well as greater than about 12 phenolic cycles. Examples of such embodiments can include, for example, the flavolans, in the class of condensed tannins.

In some embodiments, the phenolic compounds are natural phenols that can be enzymatically polymerized. Derivatives of natural phenols can also be used in some embodiments. These embodiments can include phenolic compounds having less than 12 phenolic groups, such that they can range from monophenols to oligophenols. In some embodiments, the natural phenols are found in plants, have an antioxidant activity, or a combination thereof. Examples of the natural phenols include, for example, catechol- and resorcinol-types (benzenediols) with two phenolic hydroxy groups, and pyrogallol- and phloroglucinol-types (benzenetriols) with three hydroxy groups. Natural phenols may have heteroatom substituents other than hydroxyl groups, ether and ester linkages, carboxylic acid derivatives, or some combination thereof. In some embodiments, the natural phenols include natural phenol drugs and their derivatives. Examples of such drugs include, but are not limited to, anthraquinone drugs, flavone drugs, and flavonol drugs. Examples of anthraquinone drugs include, but are not limited to, aloe emodin, aquayamycin, and diacerein. Examples of flavone drugs include, but are not limited to, ansoxetine and hidrosmin. Examples of flavonol drugs include, but are not limited to, monoxerutin and troxerutin.

In some embodiments, the phenolic compound is a tannin, a polyphenolic phenylpropanoid, or a combination thereof. In some embodiments, the tannin is a hydrolysable tannin, a condensed tannin, or a combination thereof. Hydrolysable tannins can be found, for example, in chinese gall, which is almost pure in that it has no or substantially no condensed tannins. Condensed tannins can be found, for example, in green tea leaf, which is also almost pure in that it has no or substantially no hydrolysable tannins.

Examples of hydrolysable tannin can include gallotannic acids, quercitannic acids, ellagitannins, gallotannin, pentagalloyl glucose, galloylquinic acid, galloyl-shikimic acid, and punicalagin. In some embodiments, the hydrolysable tannin is a gallotannin or ellagitannin, and isomers thereof, such as isomers that can precipitate protein. Examples of gallotannins include the gallic acid esters of glucose in tannic acid ($C_{76}H_{52}O_{46}$) and pentagalloyl glucose (PGG), and isomers thereof, such as the isomers of PGG that function to precipitate proteins. Examples of an ellagitannin include castalin and punicalagin. In some embodiments, the tannin is a gallic acid ester having a molecular weight ranging from about 500 Daltons to about 3000 Daltons. In some embodiments, the tannin is a proanthocyanidin having a molecular weight of up to about 20,000 Daltons. In some embodiments, the hydrolysable tannins are derivatives of gallic acid and characterized by a glucose, quinic acid or shikimic acid core with its hydroxyl groups partially or totally esterified with gallic acid or ellagic acid groups. The compounds can have 3 to 12 galloyl residues but may be further oxidatively crosslinked and complex. Hydrolysable tannins can be readily synthesized, for example, to obtain a phenolic compound with a high number of polar functional groups that form multiple, stable hydrogen bonds between the tannin and hydrogen peroxide in the binding system.

It should be appreciated that, while hydrolysable tannins and most condensed tannins are water soluble, some very large condensed tannins are insoluble. In some embodiments, the phenolic compound can comprise a hydrolysable tannin such as, for example, burkinabin C, castalagin, castalin, casuarictin, chebulagic acid, chebulinic acid, corilagin, digallic acid, ellagitannin, gallagic acid, gallotannin, glucogallin, grandinin, hexahydroxydiphenic acid, pentagalloyl glucose, punicalagin alpha, punicalagins, raspberry ellagitannin, roburin A, stenophyllanin A, stenophyllanin A, tannate, tannic acid, tellimagrandin II, terflavin B, or 3,4,5-tri-O-galloylquinic acid.

In some embodiments, the phenolic compound can be a flavonoid which includes several thousand natural phenol compounds. Examples of the flavonoids include the flavonols, flavones, flavan-301 (catechins), flavanones, anthocyanidins, isoflavonoids, and hybrids of any combination of these compounds. In some embodiments, the phenolic compounds are the hydrolysable tannins such as, for example, gallic acid. In some embodiments, the phenolic compounds are the lignins such as, for example, cinnamic acid. In some embodiments, the phenolic units can be dimerized or further polymerized to form any of a variety of hybrids. For example, ellagic acid is a dimer of gallic acid and forms the class of ellagitannins, or a catechin and a gallocatechin can combine to form theaflavin or the large class of thearubigins found in tea. In another example, a flavonoid and a lignan can combine to form a hybrid, such a flavonolignans.

In some embodiments, the phenolic compound can be a flavan-3ol. Examples include the catechins and the catechin gallates, where the catechin gallates are gallic acid esters of the catechins. In some embodiments, the phenolic compound is a catechin or epicatechin compound (the cis- or trans-isomers). In some embodiments, the phenolic compound is (−)-epicatechin or (+)-catechin. In some embodiments, the phenolic compound is epigallocatechin (EGC) or gallocatechin (EC). In some embdiments, the phenolic compound is a catechin gallate, such as epigallocatechin gallate (EGCG)

In some embodiments, the phenolic compound can be selected from the group of flavones consisting of apigenin, luteolin, tangeritin, flavonols, isorhamnetin, kaempferol, myricetin (e.g., extractable from walnuts), proanthocyanidins or condensed tannins, and quercetin and related phenolic compounds, such as rutin.

In some embodiments, the phenolic compound can be selected from the group of flavanones consisting of eriodictyol, hesperetin (metabolizes to hesperidin), and naringenin (metabolized from naringin).

In some embodiments, the phenolic compound can be selected from the group of flavanols consisting of catechin, gallocatechin and their corresponding gallate esters, epicatechin, epigallocatechin and their corresponding gallate esters, theaflavin and its gallate esters, thearubigins, isoflavone phytoestrogens (found primarily in soy, peanuts, and other members of the Fabaceae family), daidzein, genistein, glycitein, stilbenoids, resveratrol (found in the skins of dark-colored grapes, and concentrated in red wine), pterostilbene (methoxylated analogue of resveratrol, abundant in *Vaccinium* berries), anthocyanins, cyanidin, delphinidin, malvidin, pelargonidin, peonidin, and petunidin. And, In some embodiments, the phenolic compound can be ubiquinol an electron-rich (reduced) form of coenzyme Q10.

In some embodiments, the phenolic compound can be selected from the group of carotenoid terpenoid consisting of alpha-carotene, astaxanthin (found naturally in red algae and animals higher in the marine food chain, a red pigment familiarly recognized in crustacean shells and salmon flesh/roe), beta-carotene (found in high concentrations in butternut squash, carrots, orange bell peppers, pumpkins, and sweet potatoes), canthaxanthin, lutein (found in high concentration in spinach, kiwifruit and red peppers), lycopene (found in high concentration in ripe red tomatoes and watermelons) and zeaxanthin (the main pigment found in yellow corn, also abundant in kiwifruit).

In some embodiments, the phenolic compound can be selected from the group of phenolic acids and their esters consisting of chicoric acid (another caffeic acid derivative, is found only in the medicinal herb *echinacea purpurea*), chlorogenic acid (found in high concentration in coffee (more concentrated in *robusta* than *arabica* beans, blueberries and tomatoes, and produced from esterification of caffeic acid), cinnamic acid and its derivatives, such as ferulic acid (found in seeds of plants such as in brown rice, whole wheat and oats, as well as in coffee, apple, artichoke, peanut, orange and pineapple), ellagic acid (found in high concentration in raspberry and strawberry, and in ester form in red wine tannins), ellagitannins (hydrolysable tannin polymer formed when ellagic acid, a polyphenol monomer, esterifies and binds with the hydroxyl group of a polyol carbohydrate such as glucose), gallic acid (found in gallnuts, sumac, witch hazel, tea leaves, oak bark, and many other plants), gallotannins (hydrolysable tannin polymer formed when gallic acid, a polyphenol monomer, esterifies and binds with the hydroxyl group of a polyol carbohydrate such as glucose), rosmarinic acid (found in high concentration in rosemary, oregano, lemon balm, sage, and marjoram), and salicylic acid (found in most vegetables, fruits, and herbs; but most abundantly in the bark of willow trees, from where it was extracted for use in the early manufacture of aspirin).

In some embodiments, the phenolic compound can be selected from the group of nonflavonoid phenolics consisting of curcumin (has low bioavailability, because, much of it is excreted through glucuronidation, but bioavailability can be substantially enhanced by solubilization in a lipid (oil or lecithin), heat, addition of piperine, or through nanoparticularization, flavonolignans, for example, silymarin which is a mixture of flavonolignans extracted from milk thistle), eugenol and xanthones (mangosteen, for example, is purported to contain a large variety of xanthones, some of which, like mangostin are believed to be present only in the inedible shell).

In some embodiments, the phenolic compound can have a low molecular weight (less than about 400 Daltons), selected from the group consisting of caffeic acid, gentisic acid, protocatechuic acid, phenylacetic acid, gallic acid, phloroglucinol carboxylic acid, and derivatives thereof. Such compounds can form a sufficiently soluble binding pair, and their relatively high hydroxyl group to molecular weight ratio creates favorable conditions for obtaining the intermolecular hydrogen bonds desired for the binding systems.

In some embodiments, the phenolic compounds can be from a natural extract, such as an extract of a plant or other natural product. See, for example, U.S. Published Patent Application Nos. 20100158885 and 20110070198, each of which is hereby incorporated by reference herein in its entirety. Those skilled in the art of such extracts will understand that extracts of plant materials are not typically pure in one type of phenolic compound. Plant tannin extracts, for example, typically comprise heterogenous mixtures and derivatives of the above classes.

One of skill will appreciate, given the teachings provided herein, that the polyphenol can be combined with the reactive oxygen species as a component of a water or alcohol extract of a plant tissue. In some embodiments, the plant tissue can comprise a tannin or a pseudotannin. In some embodiments, the phenolic compound is extracted from a whole or partial plant tissue selected from the group consisting of seeds and fruits; ovaries; juice; pulp; galls; husks; bark; stems; leaves; flowers; sheaths; hulls; sprouts; bulbs; hips; tubers; roots of grains; grasses; legumes; trees; vegetables; medicinal herbs; tea leaves; algaes; marine plants; and, forages. One of skill will appreciate that the type and content of phenolic compound obtained can be expected to vary with the species, season, geographical location, cultivation, and storage. Examples of plant tissues include, but are not limited to, plant tissues from the species of *Aloe, Pachycereus,* and *Opuntia*. Other examples can include, but are not limited to, Agavaceae, Cactaceae, Poaceae, Theaceae, Leguminosae, and Lythraceae. In some embodiments, the plant tissues can be selected from the group consisting of pomegranate husk, aloe vera leaves, and green tea leaves. Other examples of plant tissues can include, but are not limited to *Aloe* (*Aloe vera*), Angelica (*Angelica archangelica*), Barberry (*Berberis vulgaris*) Root Bark, Bilberry (*Vaccinium myrtillus*), Calendula (*Calendula officinalis*), Cramp bark (*Viburnum opulus*), Eleutherococcus root (*Eleutherococcus senticosus*), Kidney wood (*Eysenhardtia orthocarpa*), *Mimosa tenuiflora*, Papaya (*Carica papaya*) leaves, Pau D'Arco (*Tabebuia avellanedae*), Sassafras albidum root bark, Saw Palmatto (*Serenoa repens*), St John's wort (*Hypericum perforatum*), Valerian (*Valeriana officinalis*), Apple (*Malus domestica*), Grape (*Vitis vinifera*), Echinacea purpurea, Grape seed extract, and Blueberry (*Vaccinium corymbosum*). In some embodiments, the plant tissues are selected from the group consisting of barley germ, green tea leaves, aloe vera leaves, mung beans, carrot, cereal grains, seeds, buds, and sprouts.

Likewise, one of skill will appreciate that there are numerous reactive oxygen species that can be used in the systems taught herein, as long as the reactive oxygen species function consistent with such teachings. Hydrogen peroxide, and precursors of hydrogen peroxide, are merely examples. In some embodiments, the phenolic compounds in the compositions (i) have phenolic hydroxyl groups that are oxidizable in the presence of a reactive oxygen species and an oxidoreductase enzyme, and (ii) are soluble in a polar liquid, such as water or an alcohol, for example, or at least moderately soluble. The phenolic compounds should also be (iii) non-toxic to a subject upon administration. And, in some embodiments, the phenolic compounds should also (iv) crosslink or polymerize with itself or other phenolic compounds in the compositions taught herein.

The reactive oxygen species can be any such species known to one of skill to have the ability to combine with the polyphenol as a composition for the uses taught herein. For example, the reactive oxygen species can include, but is not limited to, the reactive oxygen species includes a component selected from the group consisting of hydrogen peroxide, superoxide anion, singlet oxygen, and a hydroxyl radical. In some embodiments, the reactive oxygen species comprises hydrogen peroxide. And, in some embodiments, the hydrogen peroxide can be combined with the tannin at a tannin: peroxide weight ratio that ranges from about 1:1000 to about 10:1. In some embodiments, the weight ratio of the tannin: peroxide ranges from about 1:1 to about 1:50. In some embodiments, the exogeneous reactive oxygen species can be generated, as hydrogen peroxide for example, from a solid hydrogen peroxide generating material selected from the group consisting of sodium percarbonate, potassium percarbonate, a carbamide peroxide, and urea peroxide.

In some embodiments, the reactive oxygen species is hydrogen peroxide or materials that release or generate hydrogen peroxide including, but not limited to, hydration of adducts of hydrogen peroxide such as carbamide peroxide, magnesium peroxide, and sodium percarbonate; amino perhydrates; superoxide dismutase decomposition of ozone, superoxides or superoxide salts; glucose oxidase and glucose, aqueous dilution of honey; $H_2O_2$ production by *lactobacillus*; catalytic quinone hydrogenation; superoxides; and, superoxide dismutase. In some embodiments, the reactive oxygen species can include peroxide ion, organic peroxides, organic hydroperoxides, peracid superoxides, dioxygenyls, ozones, and ozonides. hydrogen peroxide or materials that generate hydrogen peroxide can be obtained or derived synthetically or from plant tissues or combinations of plant tissues.

Enzymes can activate the compositions for the methods taught herein, and the systems for the methods of treatment can be designed accordingly. And, generally speaking, one of skill will appreciate that there are a wide variety of enzymes are possible and can be target site dependent. Generally, the enzymes fall into the classes of oxidoreductases. As such, there are several enzymes and isozymes that will be present at a target site and capable of bioactivating the binding systems. In some embodiments, the oxidoreductases can be categorized into about 22 classes, and the selectivity of the bioactivation of the binding system at a target site depends, at least in part, on the selectivity of the oxidoreductase at the target site. In some embodiments, the oxidoreductase can include those oxidoreductases that act on the CH—OH group of donors (alcohol oxidoreductases, for example; EC Number class 1.1). In some embodiments, the oxidoreductase can include those oxidoreductases that act on diphenols and related substances as donors (catechol oxidase, for example, EC Number class 1.10). In some embodiments, the oxidoreductase can include those oxidoreductases that act on peroxide as an acceptor (peroxidases, such as horseradish peroxidase and catalase; EC Number class 1.11). In some embodiments, the oxidoreductase can include those oxidoreductases that act on phenols as an acceptor (tyrosinases, for example; EC Number class 1.14). Examples of other useful enzymes for the teachings provided herein include, but are not limited to, glutathione peroxidase 1 and 4 (in many mammalian tissues), glutathione peroxidase 2 (in intestinal and extracellular mammalian tissues), glutathione peroxidase 3 (in plasma mammalian tissues), lactoperoxidase, myeloperoxidase (in salivary & mucosal mammalian tissues), myeloperoxidase (in neutrophil mammalian tissues), cytochrome peroxidase (in yeasts such as *Candida albicans*) and horseradish peroxidase (common to show in vitro activity). One of skill will appreciate that oxidoreductases are selective and, in some embodiments, the oxidoreductase can include an alternate enzyme that are selective for a binding system having a phenolic compound that acts as a substrate for the alternative enzyme.

In some embodiments, the oxidoreductases include monooxygenases such as, for example, phenylalaning monooxygenase, tyrosine monooxygenase, and tryptophan monooxygenase. In some embodiments, the oxidoreductases include dioxygenases such as, for example, tryptophan dioxygenase, homogentisate dioxygenase, trimethyl lysine dioxygenase, and nitric oxide synthase. In some embodiments, the oxidoreductases include peroxidases such as, for example, catalase, myeloperoxidase, thyroperoxidase. In some embodiments, the oxidoreductases act in the presence of a co-factor or co-enzyme, such as nicotinamide adenine dinucleotide phosphate (NADP) or nicotinamide adenine dinucleotide (NAD).

Methods of Making the Compositions

The design of the binding systems include (i) selecting the phenolic compound, (ii) selecting the reactive oxygen species, (iii) selecting the ratio of phenolic compound to reactive oxygen species, and (iv) selecting a carrier. In some embodiments, the phenolic compound can be derivatized or attached to another chemical moiety via a linker, or another known method such as, for example, esterification to facilitate or improve an association between the phenolic compound and the reactive oxygen species, as well as to potentially modify, solubility, tissue absorption, or toxicity.

One of skill will appreciate that, at least from the teachings provided herein, there are a vast number of components that can be selected, the selection of which is, at least in part, dependent on type of enzyme, co-enzymes, cofactors or catalysts present at the target site for the bioactivation of the system. The design of the system can include for example, (i) identifying the target site; (ii) identifying an enzyme, co-enzymes, cofactors, or catalysts present at the target site but not present at tissue surrounding the target site; (iii) selecting a binding pair for activation at the target site by the enzyme, co-enzymes, cofactors, or catalysts; and, (iv) selecting a carrier in which the binding pair is stable or substantially stable. Identifying the target site can include, for example, select a target tissue for treatment, such as a spastic tissue at which the enzyme, co-enzymes, cofactors or catalysts present. In some embodiments, the target site is a GI tissue, at which peroxidase or oxidase may be present. Identifying an enzyme, co-enzymes, cofactors, or catalysts present at the target site but not present at tissue surrounding the target site can include, for example, identifying the tissue type, as well as the presence of a microbe. Anaerobic pathogens such as *Pseudomonas* and *Vibrio*, for example, can express a peroxide or an oxidase, making these enzymes available at the target site.

After the system and environment of use are known, one of skill can select a carrier in which the composition is stable or substantially stable. In one example, the binding system can comprise a mixture of phenolic compounds in a desired ratio with hydrogen peroxide. For example, the phenolic compounds can include a mixture of a pomegranate extract and a green tea extract, and the ratio of phenolic compound to hydrogen peroxide can range from about 1:2 to about 1:20 on a wt/wt basis, which can include molar weight bases. In some embodiments, the hydrogen peroxide can be added to the phenolic compound using a concentration of about 0.01% to about 10% hydrogen peroxide solution, and any free hydrogen peroxide can remain or be removed using the teachings provided herein. One of skill can easily select the dose for a particular use, which will vary according to factors that include the environmental conditions at the site of use. In another example, the compositions can comprise a mixture of phenolic compounds in a desired ratio with hydrogen peroxide. For example, the phenolic compounds can include a mixture of a pomegranate extract and a green tea extract, and the ratio of phenolic compound to hydrogen peroxide can range from about 3:1 to about 1:3 on a wt/wt basis (e.g., molar weight). The hydrogen peroxide can be added to the phenolic compound using a concentration of about 0.01% to about 10% hydrogen peroxide. In some embodiments, a 35% hydrogen peroxide stock solution can be used as a source of hydrogen peroxide, which can be obtained from a commercially available stock solution, for example. In some embodiments, up to 60% hydrogen peroxide stock solution can be used as a source of hydrogen peroxide. In fact, higher concentrations are available, and could be used in some embodiments if handled properly. One of skill will be able to readily select, obtain and/or produce desired concentrations of hydrogen peroxide. Again, one of skill can easily select the dose for a particular use, which will vary according to factors that include environmental conditions at the site of use. In some embodiments, this formulation has worked well for uses in animals that are non-humans.

The compositions can include, for example, a weight (molar or mass) ratio of phenolic compound to reactive oxygen species that ranges from about 1:1000 to about 1000:1. In some embodiments, the ratio of phenolic compound to reactive oxygen species can range from about 1:1000 to about 500:1, from about 1:500 to about 500:1, from about 1:250 to about 500:1, from about 1:500 to about 250:1, from about 1:250 to about 250:1, from about 1:100 to about 250:1, from about 1:250 to about 100:1, from about 1:100 to about 100:1, from about 1:100 to about 50:1, from about 1:50 to about 100:1, from about 1:50 to about 50:1, from about 1:25 to about 50:1, from about 1:50 to about 25:1, from about 1:25 to about 25:1, from about 1:10 to about 10:1, from about 1:1000 to about 250:1, from about 1:1000 to about 100:1, from about 1:1000 to about 50:1, from about 1:1000 to about 25:1, from about 1:1000 to about 10:1, from about 1:1000 to about 5:1, from about 1:10 to about 1:20, from about 1:10 to about 1:30, from about 1:10 to about 1:40, from about 1:10 to about 1:50, from about 1:10 to about 1:60, from about 1:10 to about 1:70, from about 1:10 to about 1:80, from about 1:10 to about 1:90, from about 1:20 to about 1:30, from about 1:20 to about 1:40, from about 1:20 to about 1:50, from about 1:20 to about 1:60, from about 1:20 to about 1:70, from about 1:20 to about 1:80, from about 1:20 to about 1:90, from about 1:30 to about 1:90, or any range therein.

In some embodiments, the composition comprises a ratio of a tannin and hydrogen peroxide, a phenylpropanoid and a hydrogen peroxide, a catechin and hydrogen peroxide, an epigallic acid and a hydrogen peroxide, or a combination thereof an of these phenolic compounds with hydrogen peroxide.

In some embodiments, the compositions include a stable hydrogen bonded complex between the phenolic compound and the reactive oxygen species. For example, a highly hydroxylated polyphenol compound can be combined with a high concentration of hydrogen peroxide, the combination leading to binding the hydrogen peroxide to the phenolic compound to produce the binding system. The binding system can be intended for dilution in water or a solid excipient. One of skill will appreciate that such a complex can be referred to as a polyphenol peroxysolvate, in some embodiments, when in a liquid form for storage or administration to a subject, and a phenolic perhydrate when in an anhydrous, or substantially anhydrous, form for storage or administration to a subject.

The compositions can be carried in a liquid, powder, capsule, tablet, or gas for administration to a subject. The selection of the phenolic compound should take into consideration the manner in which the reactive oxygen species will bind to the phenolic compound to form a stable, or substantially stable, binding pair. The binding pair can be considered substantially stable where the reactive oxygen species retains all, most, or at least a predictable amount of oxidation strength for the uses and functions recited herein.

One of skill will appreciate that a phenolic compound can be derivatized to introduce or enhance a desired function. The phenolic compound can be derivatized, for example, to increase it's functionality for binding to the reactive oxygen species, maintaining stability or miscibility in a carrier, or binding to a target site, using any method known to one of skill. In some embodiments, the phenolic compound can be bound to a polyol, pegylated, attached to a saccharide, or attached to glucose, for example.

Moreover, one of skill will appreciate that the compositions should, in some embodiments, be produced free of compounds that can lead to degradation of the otherwise stable, or substantially stable, combinations. As such, in some embodiments, the compositions comprise solutes that are substantially free of transition metals, metal ions, heavy metals, oxidoreductase enzymes, other strong oxidizers, reactive halogen compounds, hydrogen halides, and other compounds that can cause a decomposition of the reactive oxygen species, or its disassociation from the phenolic compound with which it forms a binding pair.

The compositions can be made using ingredients from commercially available chemical providers, or they can be made directly from whole, plant extracts, for example, water extracts or alcohol extracts.

A Commercially Available Source of the Phenolic Component

Commercially available chemical providers, for example Sigma-Aldrich, can provide phenolic and polyphenolic chemicals for use with the methods of treatment taught herein. In the example set forth below, (i) gallic acid (a model polyphenol building block) is combined with hydrogen peroxide; and, (ii) tannic acid (a model polyphenol component) is combined with hydrogen peroxide. Both gallic acid and tannic acid are commercially available from Sigma-Aldrich. One of skill will appreciate that a wide variety of polyphenolics are commercially available.

A Whole, Plant Extract as a Source of the Phenolic Component

The method of obtaining the phenolic component, e.g, the polyphenol component, from a plant tissue can be produced using the following process:
  i. Harvest plant tissue comprising a polyphenol component, for example, the polyphenol comprising a tannin. It is desirable to harvest while minimizing physical damage to the plant tissue. For example, whole leaf extractions can be performed to avoid physical damage to the leaves, but it may be desirable to reduce the size of the leaves by cutting them, for example, to increase the speed and yield of the extraction in some embodiments.
  ii. Denaturing all, or substantially all, of the oxidoreductase enzymes in the plant. This can be done through drying, for example, using heating in the range of about 60° C. to about 150° C., or a combination of such heating and dessication. Alcohols can also be used to denature the enzymes.
  iii. Extracting the polyphenols from the plant tissue using a suitable solvent including, but not limited to, water or an alcohol. Water extractions have been used in this example. Since we're after water soluble plant materials, a simple water extraction is sufficient to provide the plant extract containing polyphenols for the compositions.

The plant extraction procedures are simple, although they can be modified for efficiency in product yield and activity. Although inefficient, the simplest extraction procedure, for example, would be to merely harvest the plant tissue, denature the endogeneous enzymes, and soak the tissue in water to isolate the water soluble extract of the plant tissue. Another simple extraction method would be to harvest the plant tissue, and isolate the water soluble extract of the tissue in water at temperatures greater than about 80° C. to steam. An even simpler process would not include denaturing the enzymes, but the stability and activity of the extract in the composition suffers greatly. Additional steps can be added, however, to increase the efficiency of the extraction, although such steps are not required. For example, the harvesting can include cutting into as large of pieces as practical to the size of the plant to preserve the metabolic activity in the plant tissue can be done. The plant tissue can be pulverized after denaturing the enzymes, and the water can be heated at temperatures ranging from about 25° C. to about 100° C., from about 30° C. to about 95° C., from about 35° C. to about 90° C., from about 40° C. to about 85° C., from about 45° C. to about 80° C., from about 45° C. to about 75° C., from about 45° C. to about 70° C., from about 45° C. to about 65° C., or any amount or range therein in increments of 1° C., to make the process of extraction more efficient.

In some embodiments, the endogeneous enzymes include a catalase or peroxidase that is at least substantially inactivated. In some embodiments, the endogeneous enzymes can be inactivated through heating, cooling, boiling, freezing, dessicating, freezing and thawing cycles, blanching, or a combination thereof. In some embodiments, the endogeneous enzymes can be inactivated using a process that includes allowing natural degradation over time, adding at least 1% salt, radiating, or adding an exogeneous chemical enzymatic inhibitor.

In some embodiments, the plant extract is produced from a process comprising: harvesting the plant tissue; at least partially inactivating an endogeneous enzyme; optionally reducing particle size of the plant tissue through cutting, avulsing, or pulverizing; creating the extracted component through a process that includes combining the plant tissue with water or alcohol for an effective time and at an effective temperature; optionally removing particles from the mixture; and, adding the reactive oxygen species to the effective, or otherwise desired, amount.

In some embodiments, the water soluble plant extract can then be optionally filtered, for example, using a filter, for example a 5 um filter in some embodiments, and hydrogen peroxide can then be added to the filtered extract to a concentration of 1% by weight of the total composition. In some embodiments, the hydrogen peroxide can be added to the extract in an amount ranging from about 0.01% to about 10% by weight of the total composition. Increasing the concentration of hydrogen peroxide added has been observed to increase the potency and stability of the resulting compositions.

After combining the reactive oxygen species with the polyphenol component, the free reactive oxygen species in the compositions can be left in the composition, or it can be removed using an enzyme, catalyst, or reducing agent. In this example, the reactive oxygen species is hydrogen peroxide, and the free hydrogen peroxide can be removed from the composition in a subsequent step contacting the free hydrogen peroxide with a hydrogen peroxide degrading enzyme, such catalase; a catalyst such as manganese dioxide, platinum, iron, or copper; or, a reducing agent such as ferric chloride, copper sulfate, or sodium hypochlorite. In some embodiments, the composition having the free hydrogen peroxide can be contacted with a metal catalyst or catalase bound to a solid non-soluble substrate. In some embodiments, the solid substrate can be a bead column or screen, for example. Likewise, the catalysts and reducing agents can be used in a similar manner to remove the free hydrogen peroxide, or any other free reactive oxygen species.

As such, the concentration of free reactive oxygen species, such as free hydrogen peroxide, remaining in the composition can range from about 0 to about 10% based on total dry weight of the composition. Moreover, in some embodiments, the total hydrogen peroxide concentration can range from about 0.001% to about 1%, from about 0.001% to about 0.1%, from about 0.01% to about 0.05%, from about 0.005% to about 5%, from about 0.007% to about 2%, from about 0.01% to about 5%, from about 0.05% to about 5%, from about 0.1% to about 5%, from about 0.2% to about 4.5%, from about 0.3% to about 4%, from about 0.4% to about 3.5%, from about 0.5% to about 3%, from about 0.6% to about 2.5%, from about 0.7% to about 2%, from about 0.001% to about 1.5%, about 1%, or any amount or range therein in increments of 0.001%. And, it should be appreciated that the concentration of free hydrogen peroxide, for example, can also be reduced, or further reduced, by dilution of the composition in various commercial formulations.

Moreover, precipitates of protein or other impurities can form at this point and can optionally be removed by additional filtration, and we often filter after we allow the solution to react for about an hour. Although not necessary, additional reactive oxygen species can be added to ensure complete saturation of hydrogen peroxide on the binding sites of the polyphenols in the extract. In this example, hydrogen peroxide was used as the reactive oxygen species, keeping track of the total hydrogen peroxide concentration.

The plant extract is combined with the reactive oxygen species, and the solution can be allowed to react for a period of time ranging from about 10 minutes to about 72 hours, in some embodiments, before diluting the composition to a desired concentration. In some embodiments, the solution can be allowed to react for a period of time ranging from about 1 minute to about 96 hours, from about 5 minutes to about 48 hours, from about 10 minutes to about 36 hours, from about 10 minutes to about 24 hours, from about 10 minutes to about 12 hours, from about 10 minutes to about 8 hours, or from about 10 minutes to about 1 hour, or any range therein in increments of 1 minute. In this example, the extracts were allowed to react with the hydrogen peroxide for a minimum of 2 hours. The dilution can be desirable, for example, (i) to control the concentration of the composition in solution, and/or (ii) to accelerate degradation of the unbound reactive oxygen species to limit the composition to having no, or substantially no, free reactive oxygen species. In this example, the hydrogen peroxide is more susceptible to degradation when free in solution, and one of skill will appreciate that the degradation will increase in rate when the composition is diluted.

In some embodiments, dry compositions are provided. For example, the system can be in the form of a powder, pill, tablet, capsule, or as separate dry components for mixing into a liquid form. In these embodiments, both the phenolic compound and the reactive oxygen species are in a dry form either before or after creation of the binding pair, and the binding system can be used in the dry form, or converted to a liquid form, for any of the uses taught herein. The advantages of the dry compositions can include, for example, the ease of storage and transport. In some embodiments, the binding systems, whether in liquid or dry form, can be combined with vitamins, electrolytes, and/or other nutrients in either liquid or dry form. The dry form of the binding system can be manufactured using any drying process known to one of skill, such as solvent exchange, vacuum drying, critical point drying, heating, dessication, or a combination thereof. In some embodiments, the phenolic compound is dried as a single component. In some embodiments, the binding pair is formed, and the binding pair is dried together. And, in some embodiments, the reactive oxygen species can be, independently, in any dry form known to one of skill, such as the dry forms taught herein. In embodiments having the reactive oxygen species in an independent dry form, the dry phenolic compound and the dry reactive oxygen species can be combined in a polar solvent, for example, to create the binding pair prior to use.

Methods of Using the Compositions

Methods of treating gastrointestinal spasms are provided. This can include reducing or eliminating abdominal pain, bloating, forceful defecation, forceful vomiting, defecation urgency, constipation, and/or incontinence. Causes of gastrointestinal cramping can range from mild conditions to serious conditions, such as food poisoning, constipation, gastroenteritis, viral infections, bacterial infections, lactose intolerance, excessive flatulence and bloating, indigestion, diverticulitis, autoimmune disease, intestinal inflammation and even colorectal cancer, adhesions, and the like. In some embodiments, stress and/or dehydration can even trigger gastrointestinal cramps, for example.

The disorders treated can be self-induced. In some embodiments, gastrointestinal spasms can be self-induced through overindulging, such as through overeating and/or overdrinking. In some embodiments, gastrointestinal spasms can be due to deficiencies, such as deficiencies in nutrition or hydration, for example. The compositions taught herein can be used in treating such conditions, either alone or in co-administrations with nutritional therapy or rehydration therapies. The disorders might also be induced through environmental conditions, exercise, or socioeconomic conditions. In some embodiments, the composition can be co-administered with at least one other nutritional and/or rehydrating agent for aiding recovery from a health imbalance, or to maintain a health balance. Examples of rehydrating agents can include, but are not limited to, GATORADE and other electrolyte drinks, oral rehydration solutions (ORSs) generally, new oral rehydration solution (N-ORS), SEURO ORAL, PEDIAONE, and PEDIALYTE. Examples of nutritional supplements can include, but are not limited to, zinc sulfate, salted rice water, salted yogurt-based drinks, and vegetable or chicken soup with salt. Such health imbalances can include, but is not limited to, dehydration, malnutrition, electrolyte imbalance, vitamin deficiency, food hypersensitivities, stress induced diarrhea, abdominal cramping, and alcohol hangover, or a combination thereof. In some embodiments, the methods taught herein can further include the administration of oral rehydrating or nutritional agents such as sodium, potassium, dextrose, fructose, glucose, magnesium, zinc, selenium, vitamin A, Vitamin D, Vitamin C, dietary fiber, and combinations thereof. The amounts and ratios of the agents to the composition can be substantially varied to provide prophylaxis, therapy or maintenance of healthful balance. Ratios of the compositions herein to the nutritional agents or rehydration agents can range, for example, from about 1:100 to about 100:1, from about 1:50 to about 50:1, from about 1:40 to about 40:1, from about 1:30 to about 30:1, from about 1:20 to about 20:1, from about 1:10 to about 10:1, from about 1:5 to about 5:1, from about 1:4 to about 4:1, from about 1:3 to about 3:1, from about 1:2 to about 2:1, from about 1:1.5 to about 1.5:1, about 1:1, or any range therein. The ratios can be based on volume:volume, mass:volume, volume:mass, mass:mass, or molar:molar. It should be appreciated that the concentrations of the compositions taught herein can be the same or different than the concentrations of the nutritional agents or rehydration agents. And, it should also be appreciated that the concentrations and ratios of concentrations can be subjective to a particular administration, such that they can be independently selected according to the condition treated, objective sought, desired effect, and/or personal preference. The combinations can be administered under any regime taught herein for the administration of an agent or combination of agents.

Irritable bowel syndrome (IBS) is a problem of particular interest and includes, for example, chronic or frequent gastrointestinal spasms. IBS is often diagnosed as a set of these symptoms, such as diarrhea, constipation, and bloating, in addition to, perhaps, a measured food sensitivity. The compositions taught herein, however, can generally be used for this and other medicinal purposes, as a health supplement, or a nutritional composition. The compositions can provide a therapeutic and/or prophylactic effect in the treatment of a condition in a subject, particularly in the treatment of a gastrointestinal spasm. The targeted action of the binding systems allows for the administration of surprisingly low effective doses of the phenolic compounds. As a result, the compositions also improve safety by substantially increasing the separation between an effective dose and any toxic/side effects.

The terms "treat," "treating," and "treatment" can be used interchangeably and refer to the administering or application of the binding systems taught herein, including such administration as a health or nutritional supplement, and all administrations directed to the prevention, inhibition, amelioration of the symptoms, or cure of a condition taught herein. The terms "disease," "condition," "disorder," and "ailment" can be used interchangeably in some embodiments. The term "subject" and "patient" can be used interchangeably and refer to an animal such as a mammal including, but not limited to, non-primates such as, for example, a cow, pig, horse, cat, dog, rat and mouse; and primates such as, for example, a monkey or a human. As such, the terms "subject" and "patient" can also be applied to non-human biologic applications including, but not limited to, veterinary, companion animals, commercial livestock, aquaculture, and the like. Many of the applications can include control environmental pathogens that are on or in plants, as well as places not necessarily in living hosts, such as those that are in water and water systems, for example, as well as soil, air, and food for microbial control, alteration of surface characteristics, or anywhere that can benefit from a supply of a stable oxidizer source.

In some embodiments, the composition includes (i) a phenolic compound selected from the group consisting of condensed tannins, hydrolysable tannins, complex tannins, phlorotannins, psuedotannins, and derivatives thereof; and, (ii) hydrogen peroxide in a stable, or substantially stable, non-covalent association.

In some embodiments, the compositions taught herein can be used to protect, maintain, improve, or restore a digestive health of a subject when administered orally in an effective amount. In some embodiments, the effectiveness can be measured by comparing to a control group that did not receive the binding system. And, in some embodiments, the effectiveness can be measured according to a historical baseline for the subject being treated. The binding systems can be used to prevent, inhibit, or ameliorate the symptoms associated with a loss of digestive tract homeostasis. In some embodiments, the binding systems can be used to prevent, treat, ameliorate the symptoms of, or even cure, a chronic gastrointestinal condition. Such conditions can include, but are not limited to, hyperacidity, colitis, irritable bowel syndrome, crohn's disease, necrotic enteritis, functional colonic diseases, malabsorption, a peptic ulcer, gastroesophageal reflux disease, ulcerative colitis, and diverticulitis. In some embodiments, the binding systems can be used to reduce mucosal tissue inflammation, dysfunction, or damage. Such conditions can be induced, for example, by drug side effects, chemotherapy, dysbiosis, radiation, changes in normal flora, hyperimmunity, autoimmune reactions, immune deficiencies, nervousness, allergies, chemical irritation, and stress. In some embodiments, the binding systems can be administered for selectively inhibiting the growth of gastrointestinal pathogens. It should be appreciated that there may be lesser inhibition of non-pathogenic strains, particularly common probiotic bacteria such as bifidobacteria and lactobacilli. And, in some embodiments, administration of the binding systems can produce short term immune modulation effects as well as potentially change the chronic expression of the activating enzymes associated with some conditions with longer term use of the binding systems.

In some embodiments, the symptoms of a gastrointestinal condition can include, for example, diarrhea, dehydration, malnutrition, constipation, nausea, and/or cramping. And, in some embodiments, the symptoms of a gastrointestinal condition can be temporary and include acid irritation, indigestion, bloating, cramps, spasmodic peristalsis, diarrhea, and constipation. Administering the binding systems for the treatment and/or management of gastrointestinal conditions can be considered a nutritional or health supplement, in some embodiments. In some such embodiments, for example, the binding pair can be administered to prevent, inhibit, or ameliorate the effect, infectivity, and virulence of pathogens including bacteria, virus, fungi, yeast, prions, protozoa and parasites in a subject orally taking an effective amount of the supplement.

As described herein, the binding systems can be used in a method of treating acute diarrhea in a subject. In some embodiments, the methods comprise orally administering an effective amount of a binding system taught herein to the subject. The binding system can prevent, inhibit, or ameliorate a symptom of acute diarrhea in the subject when compared to a second subject in a control group in which the binding system was not administered. In some embodiments, the symptom is selected from the group consisting of a stool score, heartburn, indigestion, urgency of defecation, nausea, vomiting, stomach pain, and bloating.

As described herein, the binding systems can be used in a method of treating irritable bowel syndrome in a subject. In some embodiments, the method comprises orally administering an effective amount of a binding system taught herein to the subject. The binding system can prevent, inhibit, or ameliorate the symptoms of irritable bowel syndrome in the subject when compared to a second subject in a control group in which the binding system was not administered. In some embodiments, the symptom is selected from the group consisting of a stool score, heartburn, indigestion, urgency of defecation, nausea, vomiting, stomach pain, and bloating.

As described herein, the binding systems can be used in a method of treating an inflammatory bowel disease in a subject. In some embodiments, the method comprises orally administering an effective amount of a binding system taught herein to the subject. The binding system can prevent, inhibit, or ameliorate the symptoms of inflammatory bowel disease in the subject when compared to a second subject in a control group in which the binding system was not administered. In some embodiments, the symptom is selected from the group consisting of a stool score, heartburn, indigestion, urgency of defecation, nausea, vomiting, stomach pain, and bloating.

As described herein, the binding systems can be used in a method of treating food poisoning in a subject. In some embodiments, the method comprises orally administering an effective amount of a binding system taught herein to the subject. The binding system can prevent, inhibit, or ameliorate the symptoms of food poisoning in the subject when compared to a second subject in a control group in which the binding system was not administered. In some embodiments, the symptom is selected from the group consisting of a stool score, heartburn, indigestion, urgency of defecation, nausea, vomiting, stomach pain, and bloating.

Methods of Administering the Compositions

The terms "administration" or "administering" can be used to refer to a method of incorporating a composition into the cells or tissues of a subject, either in vivo or ex vivo to test the activity of a system, as well as to diagnose, prevent, treat, or ameliorate a symptom of a disease. In one example, a compound can be administered to a subject in vivo using any means of administration taught herein. In another example, a compound can be administered ex vivo by combining the compound with cell tissue from the subject for purposes that include, but are not limited to, assays for determining utility and efficacy of a composition. And, of course, the systems can be used in vitro to test their stability, activity, toxicity, efficacy, and the like. When the compound is incorporated in the subject in combination with one or active agents, the terms "administration" or "administering" can include sequential or concurrent incorporation of the compound with the other agents such as, for example, any agent described above. A pharmaceutical composition of the invention can be formulated, in some embodiments, to be compatible with its intended route of administration.

Any administration vehicle known to one of skill to be suitable for administration of the compounds, compositions, and formulations taught herein can be used. A "vehicle" can refer to, for example, a diluent, excipient or carrier with which a compound is administered to a subject. A "pharmaceutically acceptable carrier" is a diluent, adjuvant, excipient, or vehicle with which the composition is administered. A carrier is pharmaceutically acceptable after approval by a state or federal regulatory agency or listing in the U.S. Pharmacopeial Convention or other generally recognized sources for use in subjects. The pharmaceutical carriers include any and all physiologically compatible solvents, dispersion media, coatings, antibacterial and antifungal agents, isotonic and absorption delaying agents, and the like. Examples of pharmaceutical carriers include, but are not limited to, sterile liquids, such as water, oils and lipids such as, for example, phospholipids and glycolipids. These sterile liquids include, but are not limited to, those derived from petroleum, animal, vegetable or synthetic origin such as, for example, peanut oil, soybean oil, mineral oil, sesame oil, and the like. Suitable pharmaceutical excipients include, but are not limited to, starch, sugars, inert polymers, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain minor amounts of wetting agents, emulsifying agents, pH buffering agents, or a combination thereof. The compositions can take the form of solutions, suspensions, emulsion, tablets, pills, capsules, powders, sustained-release formulations and the like. Oral formulations can include standard carriers such as, for example, pharmaceutical grades mannitol, lactose, starch, magnesium stearate, sodium saccharine, cellulose, magnesium carbonate, and the like. See Martin, E.W. Remington's Pharmaceutical Sciences. Supplementary active compounds can also be incorporated into the compositions. In some embodiments, the carrier can be a solvent or dispersion medium including, but not limited to, water; ethanol; a polyol such as for example, glycerol, propylene glycol, liquid polyethylene glycol, and the like; and, combinations thereof. The proper fluidity can be maintained in a variety of ways such as, for example, using a coating such as lecithin, maintaining a required particle size in dispersions, and using surfactants.

The compositions can be administered to a subject orally or rectally, for example, in the treatment of a gastrointestinal spasm. Oral administration can include digestive tract, buccal, sublingual, and sublabial, and a carrier such as a solid or liquid can be used. A solid can include, for example, a pill, capsule, tablet, or time-release technology in some embodiments; and, for buccal or sublingual, a solid can include an orally disintegrating tablet, a film, a lollipop, a lozenge, or chewing gum; and, a liquid can include a mouthwash, a toothpaste, an ointment, or an oral spray. A liquid can include, for example, a solution, soft gel, suspension, emulsion, syrup, elixir, tincture, or a hydrogel.

Tablets, pills, capsules, troches liquids and the like may also contain binders, excipients, disintegrating agent, lubricants, glidants, chelating agents, buffers, tonicity modifiers, surfactants, sweetening agents, and flavoring agents. Some examples of binders include microcrystalline cellulose, gum tragacanth or gelatin. Some examples of excipients include starch or maltodextrin. Some examples of disintegrating agents include alginic acid, corn starch and the like. Some examples of lubricants include magnesium stearate or potassium stearate. An example of a chelating agent is EDTA. Some examples of buffers are acetates, citrates or phosphates. Some examples of tonicity modifiers include sodium chloride and dextrose. Some examples of surfactants for micellation or increasing cell permeation include coconut soap, anionic, cationic or ethoxylate detergents. An example of a glidant is colloidal silicon dioxide. Some examples of sweetening agents include sucrose, saccharin and the like. Some examples of flavoring agents include peppermint, chamomile, orange flavoring and the like. It should be appreciated that the materials used in preparing these various compositions should be pharmaceutically pure and non-toxic in the amounts used Rectal administrations can be made using any method known to one of skill. For example, a suppository formulation can be prepared by heating glycerin to about 120° C., combining the binding system with the heated glycerin, mixing the combination, adding purified water to a desired consistency, and pouring the desired consistency into a mold to form the suppository.

The compositions may be administered as suspensions or emulsions. Lipophilic solvents or vehicles include, but are not limited to, fatty oils such as, for example, sesame oil; synthetic fatty acid esters, such as ethyl oleate or triglycerides; and liposomes. Suspensions that can be used for injection may also contain substances that increase the viscosity of the suspension such as, for example, sodium carboxymethyl cellulose, sorbitol, or dextran. Optionally, a suspension may contain stabilizers or agents that increase the solubility of the compounds and allow for preparation of highly concentrated solutions. In some embodiments, an administration, such as an oral or rectal administration, for example, may include liposomes. In some embodiments, the liposome may assist in a targeted delivery system. The liposomes can be designed, for example, to bind to a target protein and be taken up selectively by the cell expressing the target protein.

In some embodiments, isotonic agents can be used such as, for example, sugars; polyalcohols that include, but are not limited to, mannitol, sorbitol, glycerol, and combinations thereof; and sodium chloride. Sustained absorption characteristics can be introduced into the compositions by including agents that delay absorption such as, for example, monostearate salts, gelatin, and slow release polymers. Carriers can be used to protect against rapid release, and such carriers include, but are not limited to, controlled release formulations in implants and microencapsulated delivery systems. Biodegradable and biocompatible polymers can be used such as, for example, ethylene vinyl acetate, polyanhydrides, polyglycolic acid, collagen, polyorthoesters, polylactic acid, polycaprolactone, polyglycolic copolymer, and the like. Such formulations can generally be prepared using methods known to one of skill in the art.

In some embodiments, the composition is administered in a sustained release formulation, and the formulation can include one or more agents in addition to the composition. In some embodiments, the sustained release formulations can reduce the dosage and/or frequency of the administrations of such agents to a subject. In some embodiments, an exogenous catalyst or enzyme is introduced to a target and one or more of the reactive oxygen species, phenolic compound, or the exogenous catalyst or enzyme are segregated by encapsulation or micellation to delay the bioactivation until target site is reached by all components.

One of skill understands that the amount of the agents administered can vary according to factors such as, for example, the type of disease, age, sex, and weight of the subject, as well as the method of administration. For example, an administration can call for substantially different amounts to be effective. Dosage regimens may also be adjusted to optimize a therapeutic response. In some embodiments, a single bolus may be administered; several divided doses may be administered over time; the dose may be proportionally reduced or increased; or, any combination thereof, as indicated by the exigencies of the therapeutic situation and factors known one of skill in the art. It is to be noted that dosage values may vary with the severity of the condition to be alleviated, as well as whether the administration is prophylactic, such that the condition has not actually onset or produced symptoms. Dosage regimens may be adjusted over time according to the individual need and the professional judgment of the person administering or supervising the administration of the compositions, and the dosage ranges set forth herein are exemplary only and do not limit the dosage ranges that may be selected by medical practitioners. The compounds can be administered in dosage units. The term "dosage unit" can refer to discrete, predetermined quantities of a compound that can be administered as unitary dosages to a subject. A predetermined quantity of active compound can be selected to produce a desired therapeutic effect and can be administered with a pharmaceutically acceptable carrier. The predetermined quantity in each unit dosage can depend on factors that include, but are not limited to, (a) the unique characteristics of the active compound and the particular therapeutic effect to be achieved, and (b) the limitations inherent in the art of creating and administering such dosage units.

An "effective amount" of a compound can be used to describe a therapeutically effective amount or a prophylactically effective amount. An effective amount can also be an amount that ameliorates the symptoms of a disease. A "therapeutically effective amount" can refer to an amount that is effective at the dosages and periods of time necessary to achieve a desired therapeutic result and may also refer to an amount of active compound, prodrug or pharmaceutical agent that elicits any biological or medicinal response in a tissue, system, or subject that is sought by a researcher, veterinarian, medical doctor or other clinician that may be part of a treatment plan leading to a desired effect. In some embodiments, the therapeutically effective amount should be administered in an amount sufficient to result in amelioration of one or more symptoms of a disorder, prevention of the advancement of a disorder, or regression of a disorder. In some embodiments, for example, a therapeutically effective amount can refer to the amount of an agent that provides a measurable response of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired action of the composition.

In some embodiments, the desired action of the composition is relief of a gastrointestinal spasm. The relief can include, for example, reducing or eliminating abdominal pain, bloating, forceful defecation, forceful vomiting, defecation urgency, constipation, and/or incontinence. In these embodiments, at least 10% relief can be obtained in a time ranging from 1 minute to 24 hours, from about 5 minutes to about 18 hours, from about 10 minutes to about 12 hours, from about 20 minutes to about 8 hours, from about 30 minutes to about 6 hours, from about 1 hours to about 4 hours, from about 2 hours to about 10 hours, from about 3 hours to about 9 hours, or any range or amount therein in increments of 5 minutes.

A "prophylactically effective amount" can refer to an amount that is effective at the dosages and periods of time necessary to achieve a desired prophylactic result, such as prevent the onset of an inflammation, allergy, nausea, diarrhea, infection, and the like. Typically, a prophylactic dose is used in a subject prior to the onset of a disease, or at an early stage of the onset of a disease, to prevent or inhibit onset of the disease or symptoms of the disease. A prophylactically effective amount may be less than, greater than, or equal to a therapeutically effective amount.

In some embodiments, a therapeutically or prophylactically effective amount of a composition may range in concentration from about 0.01 nM to about 0.10 M; from about 0.01 nM to about 0.5 M; from about 0.1 nM to about 150 nM; from about 0.1 nM to about 500 µM; from about 0.1 nM to about 1000 nM, 0.001 µM to about 0.10 M; from about 0.001 µM to about 0.5 M; from about 0.01 µM to about 150 µM; from about 0.01 µM to about 500 µM; from about 0.01 µM to about 1000 nM, or any range therein. In some embodiments, the compositions may be administered in an amount ranging from about 0.005 mg/kg to about 100 mg/kg; from about 0.005 mg/kg to about 400 mg/kg; from about 0.01 mg/kg to about 300 mg/kg; from about 0.01 mg/kg to about 250 mg/kg; from about 0.1 mg/kg to about 200 mg/kg; from about 0.2 mg/kg to about 150 mg/kg; from about 0.4 mg/kg to about 120 mg/kg; from about 0.15 mg/kg to about 100 mg/kg, from about 0.15 mg/kg to about 50 mg/kg, from about 0.5 mg/kg to about 10 mg/kg, or any range therein, wherein a human subject is often assumed to average about 70 kg.

The amount of the composition administered may vary widely depending on the type of formulation, size of a unit dosage, kind of excipients, and other factors well known to those of ordinary skill in the art. A formulation may comprise, for example, an amount of the composition ranging from about 0.0001% to about 6% (w/w), from about 0.01% to about 1%, from about 0.1% to about 0.8%, or any range therein, with the remainder comprising the excipient or excipients. In some embodiments, the compositions can be administered, for example, in an amount of ranging from about 0.1 µg/kg to about 1 mg/kg, from about 0.5 µg/kg to about 500 µg/kg, from about 1 µg/kg to about 250 µg/kg, from about 1 µg/kg to about 100 µg/kg from about 1 µg/kg to about 50 µg/kg, or any range therein. One of skill can readily select the frequency and duration of each administration. For example, depending on the gastrointestinal disorder treated, whether a prophylactic treatment or a treatment of an existing disorder, variables such as the age and size of the subject can be considered, as well as the source and type of the polyphenol component and the intensity of the symptoms. In these embodiments, the compositions can be administered orally in daily doses ranging from about 5 µg to about 5000 µg dry weight, for example. In such embodiments, the compositions can be administered orally in amounts ranging from about 5 µg to about 5000 µg, from about 10 µg to about 4000 µg, from about 20 µg to about 3000 µg, from about 50 µg to about 2000 µg, from about 100 µg to about 1000 µg, from about 250 µg to about 500 µg, or any range therein, in dry weight. In some embodiments, the compositions can be administered orally in daily doses of about 100 µg, about 200 µg, about 300 µg, about 400 µg, about 500 µg, about 600 µg, about 700 µg, about 800 µg, about 900 µg, about 1000 µg, about 2000 µg, about 3000 µg, about 4000 µg, about 5000 µg, about 6000 µg, about 7000 µg, about 8000 µg, about 9000 µg, or any range therein in increments of 50 µg dry weight.

In some embodiments, the composition can be administered in conjunction with at least one other therapeutic agent for the condition being treated. The amounts of the agents can be reduced, even substantially, such that the amount of the agent or agents desired is reduced to the extent that a significant response is observed from the subject. A significant response can include, but is not limited to, a reduction or elimination of nausea, a visible increase in tolerance, a faster response to the treatment, a more selective response to the treatment, or a combination thereof. In some embodiments, the methods taught herein can further include the administration of an antibiotic, an anti-emetic, an anticholinergic, an antispasmodic, or an anticancer agent.

Antibiotics can include, for example, aminoglycosides, ansamycins, carbacephem, carbapenems, cephalosporins (first through fifth generation), glycopeptides, lincosamides, macrolides, monobactams, penicillins, penicillin combinations, polypeptides, quinolones, sulfonamides, tetracyclines, and drugs against mycobacteria. In some embodiments, the antibiotic is selected from the group consisting of natural penicillin, cephalosporin, amoxicillin, ampicillin, clavamox, polymyxin, tetracycline, chlortetracycline, doxycycline, chloramphenicol, erythromycin, oleandomycin, streptomycin, gentamicin, kanamycin, tombramycin, nalidixic acid, rifamycin, rifampicin, prontisil, gantrisin, trimethoprim, isoniazid, para-aminosalicylic acid, and ethambutol. One of skill will appreciate that subgroups of this group can be desired in some embodiments. Anti-emetics can include, for example, anticholinergic agents, antidopaminergic agents, 5-HT3 antagonists, H1 antihistamines, cannabinoids, corticosteroids, and benzodiazepines. In some embodiments, the anti-emetics can be selected from the group consisting of benzodiazepines such as diazepam or lorazepam; 5-HT$_3$ receptor antagonists such as ondansetron, tropisetron, granisetron, and dolasetron. Antispasmodics can include, for example, anticholinergics such as dicyclomine and hyoscyamine, as well as mebeverine and papaverine, for example. Anticancer agents can include, for example, alkylating agents, antimetabolites, anthracyclines, plant alkaloids, topoisomerase inhibitors, and other antitumor agents. One of skill will appreciate that the agents listed above can be used alone, or in combination, in some embodiments. For example, chemotherapy and anti-emetics can be administered together. And, anti-emetics can be administered together, such as a combination of corticosteroids and a second anti-emetic such as an antihistamine, anticholinergic, benzodiazepine, cannabinoid, or an anti-dopaminergic agent.

Combinations therapies can be administered, for example, for 30 minutes, 1 hour, 2 hours, 4 hours, 8 hours, 12 hours, 18 hours, 1 day, 2 days, 3 days, 4 days, 5 days, 6 days, 7 days, 8 days, 9 days, 10 days, 2 weeks, 3 weeks, 4 weeks, 6 weeks, 3 months, 6 months 1 year, any combination thereof, or any amount of time considered necessary by one of skill. The agents can be administered concomitantly, sequentially, or cyclically to a subject. Cycling therapy involves the administering a first agent for a predetermined period of time, administering a second agent or therapy for a second predetermined period of time, and repeating this cycling for any desired purpose such as, for example, to enhance the efficacy of the treatment. The agents can also be administered concurrently. The term "concurrently" is not limited to the administration of agents at exactly the same time, but rather means that the agents can be administered in a sequence and time interval such that the agents can work together to provide additional benefit. Each agent can be administered separately or together in any appropriate form using any appropriate means of administering the agent or agents.

The compositions taught herein can be used in co-administrations with nutritional therapy or rehydration therapies. In some embodiments, the composition can be co-administered with at least one other nutritional and/or rehydrating agent for aiding recovery from a health imbalance, or to maintain a health balance. Examples of rehydrating agents can include, but are not limited to, GATORADE and other electrolyte drinks, oral rehydration solutions (ORSs) generally, new oral rehydration solution (N-ORS), SEURO ORAL, PEDIAONE, and PEDIALYTE. Examples of nutritional supplements can include, but are not limited to, zinc sulfate, salted rice water, salted yogurt-based drinks, and vegetable or chicken soup with salt. Such health imbalances can include, but is not limited to, dehydration, malnutrition, electrolyte imbalance, vitamin deficiency, food hypersensitivities, stress induced diarrhea, abdominal cramping, and alcohol hangover, or a combination thereof. In some embodiments, the methods taught herein can further include the administration of oral rehydrating or nutritional agents such as sodium, potassium, dextrose, fructose, glucose, magnesium, zinc, selenium, vitamin A, Vitamin D, Vitamin C, dietary fiber, and combinations thereof. The amounts and ratios of the agents to the composition can be substantially varied to provide prophylaxis, therapy or maintenance of healthful balance. Ratios of the compositions herein to the nutritional agents or rehydration agents can range, for example, from about 1:100 to about 100:1, from about 1:50 to about 50:1, from about 1:40 to about 40:1, from about 1:30 to about 30:1, from about 1:20 to about 20:1, from about 1:10 to about 10:1, from about 1:5 to about 5:1, from about 1:4 to about 4:1, from about 1:3 to about 3:1, from about 1:2 to about 2:1, from about 1:1.5 to about 1.5:1, about 1:1, or any range therein. The ratios can be based on volume:volume, mass:volume, volume:mass, mass:mass, or molar:molar. It should be appreciated that the concentrations of the compositions taught herein can be the same or different than the concentrations of the nutritional agents or rehydration agents. And, it should also be appreciated that the concentrations and ratios of concentrations can be subjective to a particular administration, such that they can be independently selected according to the condition treated, objective sought, desired effect, and/or personal preference.

The combinations can be administered under any regime taught herein for the administration of an agent or combination of agents.

Articles of Manufacture

Articles of manufacture that encompass finished, packaged and labelled products are provided. The articles of manufacture include the appropriate unit dosage form in an appropriate vessel or container such as, for example, a glass vial or other container that is hermetically sealed. In the case of dosage forms suitable for oral administration, the active ingredient, e.g. one or more agents including a dosage form taught herein, may be suitable for administration orally, rectally, or the like.

As with any such product, the packaging material and container are designed to protect the stability of the product during storage and shipment. In addition, the articles of manufacture can include instructions for use or other information material that can advise the user such as, for example, a physician, technician or patient, regarding how to properly administer the composition as a prophylactic, therapeutic, or ameliorative treatment of the disease of concern. In some embodiments, instructions can indicate or suggest a dosing regimen that includes, but is not limited to, actual doses and monitoring procedures.

In some embodiments, the articles of manufacture can comprise one or more packaging materials such as, for example, a box, bottle, tube, vial, container, sprayer, insufflator, intravenous (I.V.) bag, envelope, and the like; and at least one unit dosage form of an agent comprising an extract taught herein within the packaging material. There can be a first composition comprising at least one unit dosage form of an agent comprising a binding system as taught herein within the packaging material, and optionally, a second composition comprising a second agent such as, for example, any other bioactive agent that may be administered in combination with the binding system, or any prodrugs, codrugs, metabolites, analogs, homologues, congeners, derivatives, salts, solvates, and combinations thereof. In some embodiments, the articles of manufacture may also include instructions for using the composition as a diagnostic, prophylactic, therapeutic, or ameliorative treatment for the condition of concern. In some embodiments, the instructions can include informational material indicating how to administer the systems for a particular use or range of uses, as well as how to monitor the subject for positive and/or negative responses to the systems.

In some embodiments, the article of manufacture can include a substantially anhydrous binding system. For example, a kit can be assembled which includes the anhydrous binding system comprising an anhydrous tannin with instructions combining the tannin with and an anhydrous reactive species generating component that forms a therapeutically, prophylactically, or nutritionally useful composition upon hydration.

Kits for the treatment of gastrointestinal spasms are provided herein. In these embodiments, the kits can include the polyphenol component and/or the reactive oxygen species in a wet or dry form. Optionally, the kits can include instructions for use in treating a subject. The instructions can include, for example, instructions on diluting the composition to a desired concentration and administration according to suggested dilution factors on the basis of ages and weights of subjects, as well as known conditions and target sites. The suggested dilution factors can be selected from the ranges taught herein. In some embodiments, the kits comprise a dry, stable form of the composition components. For example, the kits can comprise a dry form of a polyphenol component, such as one polyphenol, a combination of polyphenols, or an extract of a plant tissue having polyphenols. Moreover, the kits can also comprise a dry form of a hydrogen peroxide generating material that functions to generate an effective amount of an exogenous reactive oxygen species, wherein the reactive oxygen species includes a component selected from the group consisting of hydrogen peroxide, superoxide anion, singlet oxygen, and a hydroxyl radical. In these embodiments, the composition can be at least substantially free of active endogeneous oxidative enzymes and catalytic substances that cause degradation of the composition.

Example 1. Making and Testing an Antispasmodic Composition

This experiment includes the use of gallic acid, tannic acid, a pomegranate husk extract, and a green tea extract.

Measuring the Amount of Hydrogen Peroxide that Remains Bound to the Polyphenol

One of skill knows that hydrogen peroxide does not exist in a pure, solid form under normal conditions, for example, ambient conditions. However, this example shows that the hydrogen peroxide can exist in dry form when in association with the model compounds and plant extracts, and the compositions have been isolated in a dry form as proof. Art-recognized procedures, such as those set-forth at least in U.S. Pat. Nos. 3,860,694; 3,864,454; 4,171,280; and 4,966,762, were used as a guide for this study.

The model compounds were used to show that the compounds include hydrogen peroxide, the reactive oxygen species component, in a relatively stable association with the polyphenol component. As discussed, one of skill will appreciate that hydrogen peroxide in a free form, for example, would otherwise quickly degrade. The polyphenols were provided from model compounds or plant extracts. A dry form of the compositions was made between (i) gallic acid (a model polyphenol building block from Sigma-Aldrich) and hydrogen peroxide; (ii) tannic acid (a model polyphenol component from Sigma-Aldrich) and hydrogen peroxide; (iii) pomegranate husk extract and hydrogen peroxide; and, (iv) green tea extract and hydrogen peroxide, using the procedures taught herein, including:

i. adding a solution of 35% hydrogen peroxide slowly into each of the gallic acid powder, tannic powder, pomegranate husk extract powder, or green tea extract powder. The adding is done in a glass dish or beaker at 45-65° C. under constant, gentle mixing;

ii. creating a dry form of the composition by continuing the heating under the constant, gentle mixing until fine dry granules or hard amorphous chunks form;

iii. crushing the granules or chunks into a powder, which is the dry form; dissolving the powder into water, knowing that the dry forms will not have stable, free hydrogen peroxide, such that the dissolved powder will carry only the stabilized hydrogen peroxide associated with the model compounds or extracts; and, iv. measuring the total hydrogen peroxide concentration associated with the model compounds or extracts in the dry form.

The hydrogen peroxide concentration measurements were taken using standard methods to determine the amount of hydrogen peroxide that bound to the model compounds or extracts in the dry form. It was found that (i) about 3.0% hydrogen peroxide bound to the gallic acid (a model polyphenol building block) by total dry wt; (ii) about 2.5% hydrogen peroxide bound to the tannic acid (a model polyphenol component) by total dry wt; (iii) about 1.8% hydrogen peroxide bound to the pomegranate husk extract by total dry wt; and, (iv) about 2.0% hydrogen peroxide bound to the green tea extract by total dry wt. To measure the hydrogen peroxide levels, a standard, WATERWORKS peroxide test strip method was used having a test sensitivity of 0.5, 2, 5, 10, 25, 50, 100 ppm, available from Industrial Test Systems, Inc., Rock Hill, S.C. 29730.

FIGS. 1A-1H are photographs of the dry forms of (A) gallic acid (a model polyphenol building block) bound to hydrogen peroxide; (B) gallic acid alone; (C) tannic acid (a model polyphenol) bound to hydrogen peroxide; (D) tannic acid alone; (E) pomegranate husk extract bound to hydrogen peroxide; (F) pomegranate husk extract alone; (G) green tea extract bound to hydrogen peroxide; and (H) green tea extract alone, according to some embodiments. As can be seen, the dry compositions exist and do contain a stable amount of hydrogen peroxide in an amount ranging from about 1.8% to about 3.0%, indicating the stabilizing association between the combined model compounds and extracts with the hydrogen peroxide. One of skill will appreciate that, surprisingly, the compositions contain a substantial amount of a stabilized hydrogen peroxide that is carried with the model compounds or extracts as a dry form.

The Stability of the Hydrogen Peroxide in the Combination is Greater in an Aqueous Solution than the Stability of the Hydrogen Peroxide Alone in the Aqueous Solution This method tests the stability of the hydrogen peroxide in the combination. The testing methods used follow the standard procedures set-forth by the Clinical and Laboratory Standards Institute (CLSI) and US Pharmacopeia.

i. *E. coli* was chosen as the bacteria to challenge the stability of the bound compositions and the free hydrogen peroxide.
ii. The hydrogen peroxide concentration was matched to the selected bacteria in order to form a useful curve representing hydrogen peroxide degradation over time for the samples. As such, the hydrogen peroxide was varied from 62.5 ppm to 500 ppm on a fixed *E. coli* concentration of $10^6$ CFU/ml, and a concentration of 125 ppm was chosen as the initial hydrogen peroxide level used to challenge the *E. coli* over time.
iii. A ratio of 1:1 of the hydrogen peroxide to each of the model compounds and plant extracts was used to form each bound composition, such that 125 ppm of each plant extract was combined with the 125 ppm of the hydrogen peroxide.
iv. The free hydrogen peroxide was added at a concentration of 125 ppm as a control to show the relative stability of the hydrogen peroxide alone in the aqueous solution as compared to the bound compositions.

Figure 2A:
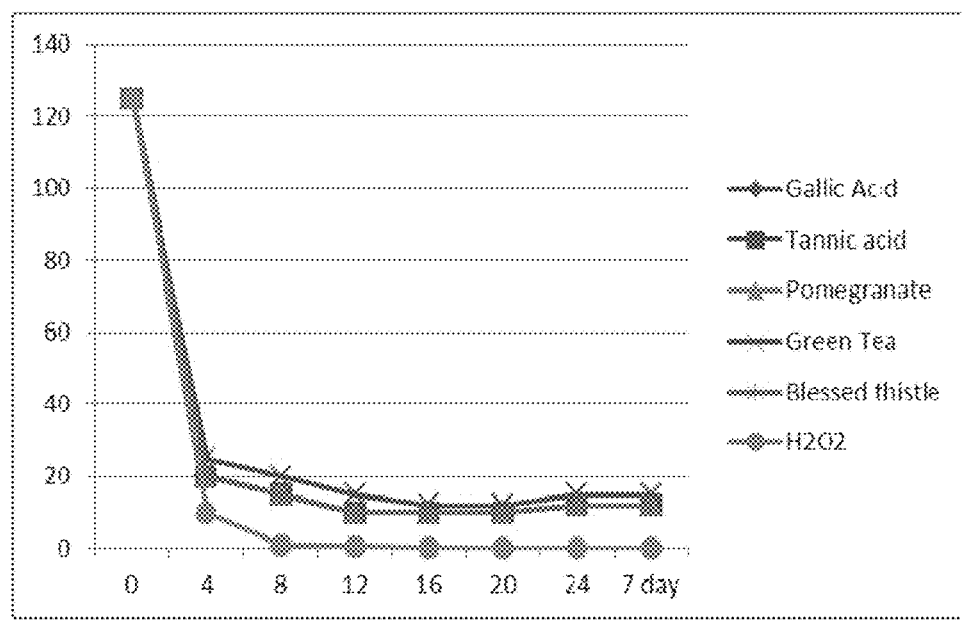
FIGS. 2A and 2B show that the stability of the hydrogen peroxide in the combination is consistently, substantially greater in an aqueous solution than the stability of the hydrogen peroxide alone in the aqueous solution, according to some embodiments.
Figure 2B:
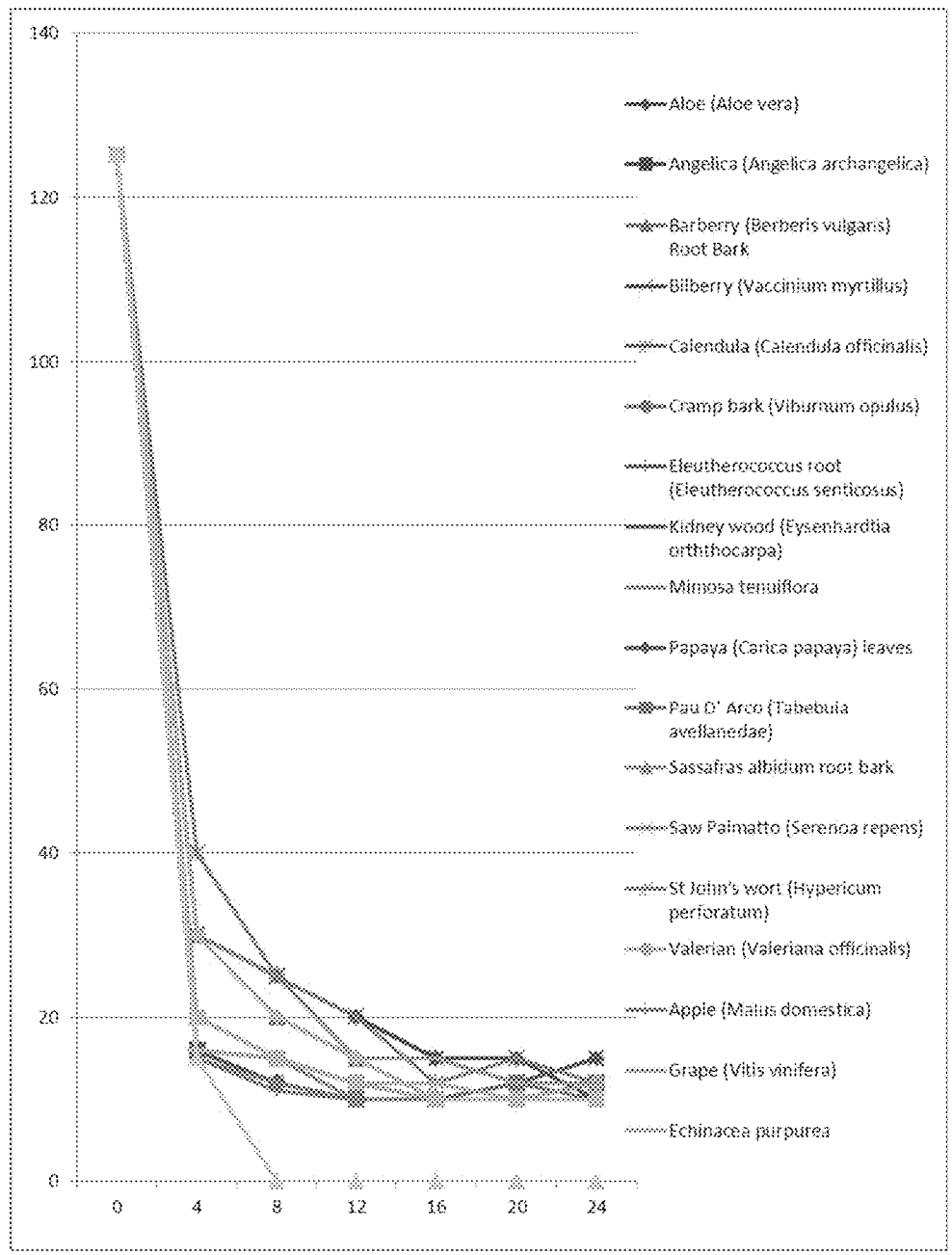

FIGS. 2A and 2B show that the stability of the hydrogen peroxide in the combination is consistently, substantially greater in an aqueous solution than the stability of the hydrogen peroxide alone in the aqueous solution, according to some embodiments. FIG. 2A compares stabilities of free hydrogen peroxide to hydrogen peroxide bound to each of: gallic acid (a model polyphenol building block), tannic acid (a model polyphenol), pomegranate husk extract, green tea extract, and Blessed thistle extract. FIG. 2B shows very similar and consistent stabilities when comparing free hydrogen peroxide to hydrogen peroxide bound to a wide variety of species of plants: *Aloe, Angelica, Barberry* Root Bark, *Bilberry, Calendula,* Cramp bark, *Eleutherococcus* root, Kidney wood, *Mimosa tenuiflora, Papaya* leaves, Pau D'Arco, *Sassafras albidum* root bark, Saw Palmatto, St. John's wort, *Valerian,* Apple, Grape, *Echinacea purpurea,* Grape seed extract, and Blueberry. In both FIGS. 2A and 2B, there are curves that cannot be identified well individually, as they are identical and overlapping. The free hydrogen peroxide curve does not overlap with any of the bound compositions beyond the 4 hour mark. Table 1 provides data used to produce the curves in the overlap for clarity.

TABLE 1

| | Hours | | | | | | |
|---|---|---|---|---|---|---|---|
| | 0 | 4 | 8 | 12 | 16 | 20 | 24 |
| Aloe (*Aloe vera*) | 125 | 30 | 25 | 20 | 15 | 15 | 10 |
| Angelica (*Angelica archangelica*) | 125 | 16 | 15 | 12 | 10 | 10 | 12 |
| Barberry (*Berberis vulgaris*) Root Bark | 125 | 30 | 20 | 15 | 10 | 10 | 12 |
| Bilberry (*Vaccinium myrtillus*) | 125 | 30 | 25 | 20 | 15 | 12 | 15 |
| Calendula (*Calendula officinalis*) | 125 | 16 | 15 | 12 | 10 | 10 | 10 |
| Cramp bark (*Viburnum opulus*) | 125 | 16 | 12 | 10 | 10 | 12 | 12 |
| Eleutherococcus root (*Eleutherococcus senticosus*) | 125 | 16 | 12 | 10 | 10 | 10 | 10 |
| Kidney wood (*Eysenhardtia orththocarpa*) | 125 | 16 | 12 | 10 | 10 | 10 | 10 |
| *Mimosa tenuiflora* | 125 | 30 | 25 | 15 | 10 | 12 | 15 |
| Papaya (*Carica papaya*) leaves | 125 | 16 | 12 | 10 | 10 | 12 | 15 |
| Pau D'Arco (*Tabebuia avellanedae*) | 125 | 20 | 15 | 10 | 10 | 12 | 10 |
| *Sassafras albidum* root bark | 125 | 20 | 15 | 10 | 10 | 10 | 12 |
| Saw Palmatto (*Serenoa repens*) | 125 | 15 | 12 | 10 | 10 | 10 | 12 |
| St John's wort (*Hypericum perforatum*) | 125 | 40 | 25 | 20 | 12 | 15 | 12 |
| Valerian (*Valeriana officinalis*) | 125 | 20 | 15 | 12 | 10 | 10 | 12 |
| Apple (*Malus domestica*) | 125 | 15 | 11 | 10 | 10 | 10 | 10 |
| Grape (*Vitis vinifera*) | 125 | 30 | 20 | 15 | 15 | 12 | 12 |
| Echinacea purpurea | 125 | 16 | 15 | 12 | 12 | 10 | 10 |
| Grape seed extract | 125 | 30 | 20 | 15 | 10 | 10 | 10 |
| Blueberry (*Vaccinium corymbosum*) | 125 | 20 | 15 | 12 | 10 | 10 | 10 |
| H2O2 | 125 | 15 | 0 | 0 | 0 | 0 | 0 |

The results were quite impressive and surprising, as the free hydrogen peroxide degraded quickly to near 0.0 ppm each time within about the first 8 hours, whereas each of the bound compositions maintained at least 10 ppm or greater for the total duration of the study, which was limited due to time constraints. As such, it was observed that the stabilities were maintained at a concentration of at least 10 ppm or greater for at least 24 hours, a concentration sufficient to maintain bactericidal activity in water. FIG. 2A shows that at least 7 days of stability remained present in at least the samples that were afforded the at least 7 days of testing. In fact, potencies have been observed to remain in the compositions when challenged for at least 30 days, and the original batches have shown to remain potent for at least 90 days, in some cases.

Example 2. Treating Gastrointestinal Spasms in Patients Having Irritable Bowel Syndrome A physician-controlled, open-label pilot study of 29 patients was performed. The patients suffered chronic gastrointestinal symptoms, including gastrointestinal spasms, and were selected because they were either non-responsive, or merely partially responsive, to standard treatments. The patients had been diagnosed with irritable bowel syndrome (IBS) and ranged in age from 29 years old to 79 years old, having a mean age of 51 years old. 83% of the patients were female. The patients were provided with sufficient volume of the composition for five days of consumption and asked to note any response or effects of the extract. Each of the patients received a 25 ml bottle of the test composition and instructed to take 5 ml per day with water at least 1 hour before meals for a 5 day period. The patients had been under treatment for chronic GI distress for an extended period and were asked to compare the performance of the test composition against their own subjective baseline health.

The Test Composition

The test solution ("the composition" or "the test composition") contained approximately 1100 micrograms total dry weight of dessicated pomegranate and green tea extract dissolved in a solution of 0.05% hydrogen peroxide in purified water. 25 ml was of the solution was then further diluted in 250 ml of oral rehydration solution to a final concentration of 0.0045% hydrogen peroxide and 100 micrograms of polyphenols before administration. Unused and undiluted solutions of the composition from the same lot were tested for hydrogen peroxide concentration using standard methodologies, described herein, verifying an unchanged ratio of peroxide to polyphenols. The free hydrogen peroxide at the fully diluted oral concentration was well below its conventionally accepted minimum inhibitory concentration for most bacteria.

The composition was tested for stability. Consistent with the methods taught herein, the composition was dessicated to a gummy solid with slow heating in a glass dish or beaker at 45-65° C. under constant, gentle mixing, along with vacuum dessication to degrade free hydrogen peroxide. The composition was then rehydrated to its original liquid volume to determine the amount of hydrogen peroxide that was stable enough to remain in the composition. And, to compare the composition to those prepared from other plant tissues, the same test was performed with a variety of polyphenol extracts including grape skin extract, guava leaf extract, green tea extract only, pomegranate rind only, Aloe vera skin extract, and knotweed extract. All of the compositions retained a substantial concentration of a stable, hydrogen peroxide through the dessication and rehydration cycle, providing evidence that water extracts from different plant sources provide a source of polyphenols that form similar stable compositions with hydrogen peroxide.

The Study

Significant responses to administration of the composition were observed. Of the 29 patients, 4 complained of constipation and 2 showed improvement. The 6 out of the 13 with gluten sensitivity (a test used in the diagnosis of IBS) reported reduced incidence of bloating, abdominal pain, bowel urgency or soft/water stools following gluten intake, suggesting that the composition is an effective treatment for irritable bowel syndrome. 19 out of the 29 (65%) subjects generally reported an improved health and relief of symptoms. 11 out of 16 (69%) of the subjects, a rather high percentage, reported improvement in gastrointestinal spasm symptoms. It has been observed, generally, that subjects receiving the composition have reported significant improvements over their historic baseline health within 24 hours.

A Literature Comparison

As described above, loperamide can be used to treat symptoms of IBS. As an agent for IBS patients, loperamide has been reported to resolve abdominal pain symptoms in 56% to 59% of patients in one study but to be no different from placebo in other studies. See, for example, Kaplan M A, et al. Arch Fam Med 8: 243-248(1999); Efskind, P S, et al. Scand J Gastroenterol 31: 463-468(1996); Cann P A, et al. Dig Dis Sci 29(3): 239-247(1984); and, Jailwala J, T F Imperiale, K Kroenke. Ann Intern Med 133: 136-147(2000). Antispasmotic medications have been reported to result in a higher level of relief of abdominal pain than placebo, with up to 56% of patients experiencing a result that was clinically meaningful. See, for example, Trinkley K E, et al. J Clin Pharm Thera 36: 275-282(2011); and, Page J G, et al. J Clin Gastroenterol 3: 153-156(1981).

In comparison, the results to date suggest that the compositions taught herein offer a significant improvement over the results that have been observed in the literature for loperamide, for example, at least with regard to the treatment of IBS.

Other Studies

Other compositions using polyphenols derived from water extractions from other plants have been tested and shown to provide similar results. In one study, grape skin extract and guava leaf extract have been combined with commercial food grade hydrogen peroxide and plant extracted hydrogen peroxide from aloe vera gel. This composition was administered to human subjects suffering from abdominal cramps. In all cases, the administration provided effective relief, evidence that other sources of water soluble polyphenol extracts provide commercially valuable and effective antispasmodic compositions.

In another study, 46 adults (including 6 having IBS) experiencing vomiting, abdominal pain, cramps, and bloating were given the 25 ml solution of the combination of composition (green tea/pomegranate/H2O2) and reported near-immediate relief with a significant reduction in symptoms remaining after 24 hours of treatment when compared to a placebo group. 78% reported significant benefit.

Example 3. Prophylactic Inhibition or Prevention of Alcohol Overindulgence

Experimental prophylactic use of the compositions has shown in a variety of subjects that it can inhibit or prevent gastrointestinal symptoms of the over consumption of alcohol. Surprisingly, it was also effective at inhibiting or preventing other symptoms of excess alcohol consumption. For example, the symptoms that have been prevented or inhibited have been measured against the historic baseline of the subject, including an alcohol-induced headache; and, alcohol-induced dermal and other tissue reactions such as apparent immune-type, allergenic reactions that included itchiness, blotchiness, flushing, red eyes, and runny nose.

Prior to the consumption of alcohol at a social event, each of the subjects consumed approximately 2000 ug-5000 ug of a green tea/pomegranate composition (dry weight) with water. The green tea/pomegranate that was administered was from a variety of lots and varied in ratio from 1:1 to 4:1 wt/wt. The subjects consumed approximately 2-10 alcoholic drinks, mixed and/or straight, ranging in content from about 5% to about 60% alcohol. The drinks ranged in content from wine to beer to liqueurs to liquors, and combinations thereof. Each of the subjects expressed that the composition provided a substantial prophylactic effect to inhibit or prevent the effects of the alcohol consumption, using their own, personal historic baselines of what they expected to experience without consuming the composition prior to drinking.

The experiments shown herein are for illustration and example only. One of skill can vary the experimental conditions and components to suit a particular or alternate experimental design. The experimental conditions can be in vitro or in vivo, or designed for any subject, for example, human or non-human. For example, animal testing can be varied to suit a desired experimental method. As such, one of skill will appreciate that the concepts can extend well-beyond the examples shown, a literal reading of the claims, the inventions recited by the claims, and the terms recited in the claims.

We claim:

1. A method of treating a treatment-resistant gastrointestinal spasm in a subject, the method comprising:
orally administering an effective amount of a formulation to treat a gastrointestinal spasm in the subject, the formulation having a binding pair in a pharmaceutically acceptable excipient; wherein, the binding pair is created by a process comprising:
selecting a water soluble tannin having a molecular weight ranging from about 170 Daltons to about 4000 Daltons; and,
oxidizing the tannin with a peroxide that is non-toxic to the subject when orally administered in the effective amount, the oxidizing including combining the tannin with the peroxide at a weight ratio ranging from about 1:1000 to about 10:1 to oxidize the tannin and form the binding pair having the oxidized tannin releasably bound to the peroxide;
wherein,
the gastrointestinal spasm is a symptom of a condition selected from the group consisting of inflammatory bowel syndrome, Crohn's disease, ulcerative colitis, diverticulitis, colorectal cancer, stress, malnutrition, necrotic enteritis, drug side-effects, chemotherapy, radiation therapy, and gastroesophageal reflux disease; and,
the formulation at least inhibits the gastrointestinal spasm when compared to a second subject in a control group in which the formulation was not administered.

2. The method of claim 1, wherein the tannin is a hydrolysable tannin.

3. The method of claim 1, wherein the tannin is a water soluble condensed tannin.

4. The method of claim 1, wherein the tannin is a flavanol.

5. The method of claim 1, wherein the tannin is a catechin.

6. The method of claim 1, wherein the tannin is gallic acid, epigallic acid, or a combination thereof.

7. The method of claim 1, wherein the tannin is a gallotannin.

8. The method of claim 1, wherein the tannin is an ellagitannin.

9. The method of claim 1, wherein the tannin is a punicalagin.

10. The method of claim 2, wherein the hydrolysable tannin is a product of a water extraction of Chinese gall.

11. The method of claim 1, wherein the tannin is a hydrolysable tannin having from 3-12 galloyl residues.

12. A method of treating a treatment resistant gastrointestinal spasm in a subject, the method comprising:
administering an effective amount of a formulation to treat a gastrointestinal spasm in the subject, the formulation having a water soluble tannin combined with a peroxide to create a binding pair prior to the administering; wherein, the binding pair is created by a process comprising:
selecting a water-soluble tannin having a molecular weight ranging from about 170 Daltons to about 4000 Daltons;
oxidizing the tannin with a peroxide that is non-toxic to the subject when orally administered in the effective amount, the oxidizing including combining the tannin with the peroxide at a weight ratio ranging from about 1:1000 to about 10:1 to form the binding pair having the oxidized tannin releasably bound to the peroxide;
wherein,
the gastrointestinal spasm is a symptom of a condition selected from the group consisting of inflammatory bowel syndrome, Crohn's disease, ulcerative colitis, diverticulitis, colorectal cancer, stress, malnutrition, necrotic enteritis, drug side-effects, chemotherapy, radiation therapy, and gastroesophageal reflux disease; and,
the formulation at least inhibits the gastrointestinal spasm when compared to a second subject in a control group in which the formulation was not administered.

13. The method of claim 12, wherein the tannin is a water soluble condensed tannin.

14. The method of claim 12, wherein the tannin is a flavanol.

15. The method of claim 12, wherein the tannin is a catechin.

16. The method of claim 12, wherein the tannin is gallic acid, epigallic acid, or a combination thereof.

17. The method of claim 12, wherein the tannin is a gallotannin.

18. The method of claim 12, wherein the tannin is an ellagitannin.

19. The method of claim 12, wherein the tannin is a punicalagin.

20. The method of claim 12, including
using a peroxide concentration ranging from about 0.001% to about 2.0% based on total dry weight of the composition;
drying the binding pair under a vacuum; and,
storing the dried binding pair for use in creating the formulation to treat irritable bowel syndrome, Crohn's disease, ulcerative colitis, diverticulitis, colorectal cancer, stress, malnutrition, necrotic enteritis, drug side-effects, chemotherapy, radiation therapy, or gastroesophageal reflux disease.

21. The method of claim 12, wherein the tannin is a hydrolysable tannin.

* * * * *